(12) United States Patent
Kuehne et al.

(10) Patent No.: US 7,691,876 B2
(45) Date of Patent: Apr. 6, 2010

(54) HETEROBICYCLIC AMIDE COMPOUNDS

(75) Inventors: Holger Kuehne, Grenzach-Wyhlen (DE); Thomas Luebbers, Loerrach (DE); Patrizio Mattei, Riehen (CH); Cyrille Maugeais, Mulhouse (FR); Philippe Pflieger, Schwoben (FR); Michelangelo Scalone, Birsfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 457 days.

(21) Appl. No.: 11/655,377

(22) Filed: Jan. 19, 2007

(65) Prior Publication Data

US 2007/0185154 A1 Aug. 9, 2007

(30) Foreign Application Priority Data

Feb. 7, 2006 (EP) .................................. 06101363

(51) Int. Cl.
*A61K 31/437* (2006.01)
*C07D 471/04* (2006.01)

(52) U.S. Cl. ...................................... 514/300; 546/113

(58) Field of Classification Search ................. 546/113; 514/300

See application file for complete search history.

(56) References Cited

U.S. PATENT DOCUMENTS

2004/0110785 A1 6/2004 Wang et al.

OTHER PUBLICATIONS

Zhang et al., J. Org. Chem., 67, pp. 2345-2347 (2002).
Le Goff et al., Pharmacology & Therapeutics, 101, pp. 17-38 (2004).
Okamoto et al., Nature, 406, pp. 203-207 (2000).

*Primary Examiner*—Patricia L Morris
(74) *Attorney, Agent, or Firm*—George W. Johnston; Dennis P. Tramaloni; Brian C. Remy

(57) ABSTRACT

Compounds of formula I

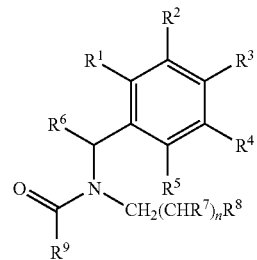

processes for their preparation and pharmaceutical compositions comprising them.

18 Claims, No Drawings

HETEROBICYCLIC AMIDE COMPOUNDS

PRIORITY TO RELATED APPLICATIONS

This application claims the benefit of European Application No. 06101363.7, field Feb. 7, 2006, which is hereby incorporated by reference in its entirety.

The present invention relates to novel heterobicyclic amide derivatives, processes for their preparation, their use as pharmaceuticals and to pharmaceutical compositions comprising them. More particularly, the present invention provides in a first aspect a compound of formula I

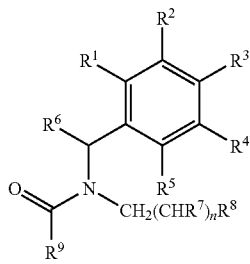

wherein $R^1$, $R^2$, $R^4$ and $R^5$ are independently from each other hydrogen, $C_1$-$C_6$alkyl, $C_1$-$C_6$alkoxy or halogen;

$R^3$ is $C_1$-$C_6$alkyl, halogen-$C_1$-$C_6$alkyl, $C_1$-$C_6$alkoxy, halogen-$C_1$-$C_6$alkoxy, aryloxy, $C_3$-$C_7$cycloalkyl, halogen-$C_3$-$C_7$cycloalkyl or pentafluorosulphuranyl; or $R^2$ and $R^3$ taken together with the carbon atoms they are attached to form a 5- or 6-membered carbocyclic ring or a 5- or 6-membered heterocyclic ring containing one or two heteroatoms selected from N, O or S;

$R^6$ is hydrogen or $C_1$-$C_6$alkyl;

$R^7$ is hydrogen, $C_1$-$C_6$alkyl, hydroxy or halogen;

$R^8$ is $C_1$-$C_6$alkyl, $C_2$-$C_6$alkenyl, halogen-$C_1$-$C_6$alkyl, heterocyclyl, heteroaryl, phenyl, —$OR^{10}$, wherein $R^{10}$ is $C_1$-$C_6$alkyl or phenyl, —$NR^{11}R^{12}$, wherein $R^{11}$ and $R^{12}$ independently from each other are selected from hydrogen, $C_1$-$C_6$alkyl, and phenyl, or —C(O)—$OR^{13}$, wherein $R^{13}$ is hydrogen or $C_1$-$C_6$alkyl;

$R^9$ is 1H-pyrrolo[2,3-c]pyridin-7-yl or 1H-pyrazolo[3,4-c]pyridin-7-yl which is unsubstituted or substituted by one or two substituents selected from halogen, $C_1$-$C_6$alkyl, halogen-$C_1$-$C_6$alkyl and C(O)OCH$_3$;

n is 1, 2 or 3;

and all pharmaceutically acceptable salts thereof.

The compounds of formula I may bear substituents within their structure, e.g. may bear appropriate 1H-pyrrolo[2,3-c]pyridin-7-yl or 1H-pyrazolo[3,4-c]pyridin-7-yl or phenyl substituents, e.g. 1H-pyrrolo[2,3-c]pyridin-7-yl may be substituted by one or two substituents selected from halogen, $C_1$-$C_6$alkyl, halogen-$C_1$-$C_6$alkyl and C(O)OCH$_3$; phenyl may be substituted by one or two groups independently selected from halogen, $C_1$-$C_6$alkyl, halogen-$C_1$-$C_6$alkyl and halogen-$C_1$-$C_6$alkoxy.

Thus, in another aspect the present invention provides a compound of formula I wherein $R^1$, $R^2$, $R^4$ and $R^5$ are independently from each other hydrogen, $C_1$-$C_6$alkyl, $C_1$-$C_6$alkoxy or halogen;

$R^3$ is $C_1$-$C_6$alkyl, $C_1$-$C_6$alkoxy, aryloxy, cycloalkyl or pentafluorosulphuranyl; or $R^2$ and $R^3$ taken together with the carbon atoms they are attached to form a 5- or 6-membered carbocyclic ring or a 5- or 6-membered heterocyclic ring containing one or two heteroatoms selected from N, O or S;

$R^6$ is hydrogen or $C_1$-$C_6$alkyl;

$R^7$ is hydrogen, $C_1$-$C_6$alkyl, hydroxy or halogen;

$R^8$ is $C_1$-$C_6$alkyl, $C_2$-$C_6$alkenyl, halogen-$C_1$-$C_6$alkyl, heterocyclyl, heteroaryl, phenyl which is unsubstituted or substituted by one or two groups independently selected from halogen, $C_1$-$C_6$alkyl, halogen-$C_1$-$C_6$alkyl and halogen-$C_1$-$C_6$alkoxy, —$OR^{10}$, wherein $R^{10}$ is $C_1$-$C_6$alkyl or phenyl, —$NR^{11}R^{12}$, wherein $R^{11}$ and $R^{12}$ independently from each other are selected from hydrogen, $C_1$-$C_6$alkyl, and phenyl, or —C(O)—$OR^{13}$, wherein $R^{13}$ is hydrogen or $C_1$-$C_6$alkyl;

$R^9$ is 1H-pyrrolo[2,3-c]pyridin-7-yl or 1H-pyrazolo[3,4-c]pyridin-7-yl which is unsubstituted or substituted by one or two substituents selected from halogen, $C_1$-$C_6$alkyl, halogen-$C_1$-$C_6$alkyl and C(O)OCH$_3$;

n is 1, 2 or 3;

and all pharmaceutically acceptable salts thereof.

The term "$C_1$-$C_6$alkyl", alone or in combination with other groups, refers to a branched or straight-chain monovalent saturated aliphatic hydrocarbon radical of one to six carbon atoms. Examples of straight-chain and branched $C_1$-$C_6$alkyl groups are methyl, ethyl, propyl, isopropyl, butyl, isobutyl, tert-butyl, the isomeric pentyls and the isomeric hexyls.

The term "$C_2$-$C_6$alkenyl", alone or in combination, means a straight-chain or branched hydrocarbon radical comprising an olefinic bond and up to 6 carbon atoms. Examples of alkenyl groups are ethenyl, 1-propenyl, 2-propenyl, isopropenyl, 1-butenyl, 2-butenyl, 3-butenyl, 2-methylpropen-1-yl and 2-methylallyl.

The term "$C_3$-$C_7$cycloalkyl" denotes a saturated carbocyclic group, such as cyclopropyl, cyclobutyl, cyclopentyl, cyclohexyl or cycloheptyl.

The term "$C_1$-$C_6$alkoxy" refers to the group R'—O—, wherein R' is $C_1$-$C_6$alkyl and the term "$C_1$-$C_6$alkyl" has the previously given significance. Examples of $C_1$-$C_6$alkoxy are methoxy, ethoxy, n-propoxy, isopropoxy, n-butoxy, isobutoxy, sec-butoxy and tert-butoxy.

The term "halogen" refers to fluorine, chlorine, bromine and iodine.

The term "halogen-$C_1$-$C_6$alkyl" refers to $C_1$-$C_6$alkyl as defined above wherein at least one of the hydrogen atoms of the $C_1$-$C_6$alkyl group is replaced by a halogen atom. Examples include trifluoromethyl, pentafluoroethyl, difluoromethyl, fluoromethyl and chlorodifluoromethyl.

The term "halogen-$C_1$-$C_6$alkoxy" refers to $C_1$-$C_6$alkoxy as defined above wherein at least one of the hydrogen atoms of the $C_1$-$C_6$alkoxy is replaced by a halogen atom. Examples include trifluoromethoxy, difluoromethoxy, fluoromethoxy, 1,1,2,2-tetrafluoroethoxy and chlorodifluoromethoxy.

The term "heteroaryl" refers to an aromatic 5- or 6-membered ring which can comprise one, two or three atoms selected from nitrogen, oxygen and/or sulphur. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, pyrrolyl, pyrazolyl or triazolyl.

The term "heterocyclyl" refers to a saturated or partly unsaturated 5- or 6-membered ring comprising one, two or three atoms selected from nitrogen, oxygen and sulphur. Examples of heterocyclyl include piperidinyl, piperazinyl, azepanyl, pyrrolidinyl, imidazolinyl, morpholinyl, thiazolidinyl, isothiazolidinyl, dihydrofuryl, tetrahydrofuryl, dihydropyranyl, tetrahydropyranyl, tetrahydrothiopyranyl and thiomorpholinyl.

The term "form a 5- or 6-membered carbocyclic ring or a 5- or 6-membered heterocyclic ring containing one or two heteroatoms selected from the group consisting of N, O or S, said carbocyclic or heterocyclic ring being unsubstituted or substituted by one, two, three or four groups independently selected from $C_1$-$C_6$alkyl, $C_3$-$C_7$cycloalkyl, $C_1$-$C_6$alkoxy, halogen, and halogen-$C_1$-$C_6$alkyl" refers to a saturated 5- or 6-membered carbocyclic ring (cyclopentyl or cyclohexyl) or a 5- or 6-membered heterocyclic ring, which contains one or two nitrogen, oxygen or sulfur atoms, such as pyrrolidinyl, thiazolidinyl, isothiazolidinyl, piperidinyl, piperazinyl, morpholinyl, thiomorpholinyl or pyranyl. Such ring may be unsubstituted or substituted by one, two, three or four groups independently selected from $C_1$-$C_6$alkyl, $C_3$-$C_7$cycloalkyl, $C_1$-$C_6$alkoxy, halogen, and halogen-$C_1$-$C_6$alkyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, e.g., hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. The compound of formula I can also be present in the form of zwitterions. In one embodiment the present invention provides a hydrochloride salt of a compound of formula I.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

Compounds of formula I can have one or more asymmetric carbon atoms and can exist in the form of optically pure enantiomers, mixtures of enantiomers such as, e.g., racemates, optically pure diastereoisomers, mixtures of diastereoisomers, diastereoisomeric racemates or mixtures of diastereoisomeric racemates. The optically active forms can be obtained, e.g., by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

In one embodiment the present invention provides compounds of formula I having the following significances independently, collectively or in any combination or sub-combination:

$R^1$, $R^2$, $R^4$, $R^5$, $R^6$ and $R^7$ are hydrogen;

$R^3$ is $C_1$-$C_6$alkyl;

$R^8$ is phenyl which is unsubstituted or substituted by one or two groups independently selected from halogen, $C_1$-$C_6$alkyl, halogen-$C_1$-$C_6$alkyl and halogen-$C_1$-$C_6$alkoxy, $R^9$ is 1H-pyrrolo[2,3-c]pyridin-7-yl or 1H-pyrazolo[3,4-c]pyridin-7-yl which is unsubstituted or substituted by one or two substituents selected from halogen, $C_1$-$C_6$alkyl, halogen-$C_1$-$C_6$alkyl and C(O)OCH$_3$;

n is 1;

and pharmaceutically acceptable salts thereof.

In another embodiment the present invention provides a compound of formula I as illustrated in formula Ia

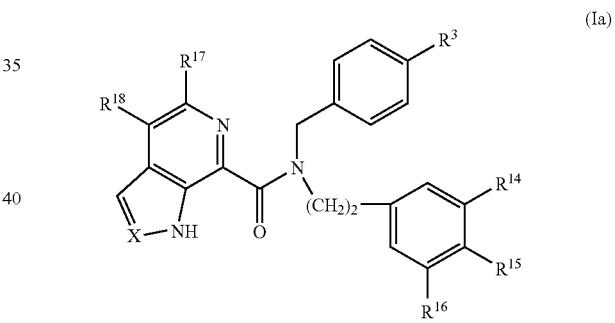

(Ia)

wherein $R^3$ is $C_1$-$C_6$alkyl;

$R^{14}$, $R^{15}$ and $R^{16}$ are independently hydrogen, halogen, $C_1$-$C_6$alkyl, halogen-$C_1$-$C_6$alkyl or halogen-$C_1$-$C_6$alkoxy, $R^{17}$ and $R^{18}$ are independently hydrogen, halogen, $C_1$-$C_6$alkyl, halogen-$C_1$-$C_6$alkyl or C(O)OCH$_3$; and X is C—H or N.

In one embodiment the present invention provides a compound of formula Ia wherein $R^3$ is $C_1$-$C_6$alkyl;

$R^{14}$ is hydrogen, halogen, halogen-$C_1$-$C_6$alkyl or halogen-$C_1$-$C_6$alkoxy;

$R^{15}$ is hydrogen, halogen or $C_1$-$C_6$alkyl;

$R^{16}$ is hydrogen or halogen;

$R^{17}$ and $R^{18}$ are independently hydrogen, halogen, $C_1$-$C_6$alkyl, halogen-$C_1$-$C_6$alkyl or C(O)OCH$_3$; and X is C—H or N.

In still another embodiment the present invention provides a compound of formula Ia wherein $R^3$ is $C_1$-$C_6$alkyl;

$R^{14}$, $R^{15}$ and $R^{16}$ are independently hydrogen, halogen, $C_1$-$C_6$alkyl, halogen-$C_1$-$C_6$alkyl or halogen-$C_1$-$C_6$alkoxy;

$R^{17}$ is hydrogen, halogen, $C_1$-$C_6$alkyl, halogen-$C_1$-$C_6$alkyl or $C(O)OCH_3$;

$R^{18}$ is hydrogen, halogen or $C_1$-$C_6$alkyl; and

X is C—H or N.

In still another embodiment the present invention provides a compound of formula Ia wherein $R^3$ is $C_1$-$C_6$alkyl;

$R^{14}$ is hydrogen, halogen, halogen-$C_1$-$C_6$alkyl or halogen-$C_1$-$C_6$alkoxy, $R^{15}$ is hydrogen, halogen or $C_1$-$C_6$alkyl;

$R^{16}$ is hydrogen or halogen;

$R^{17}$ is hydrogen, halogen, $C_1$-$C_6$alkyl, halogen-$C_1$-$C_6$alkyl or $C(O)OCH_3$;

$R^{18}$ is hydrogen, halogen or $C_1$-$C_6$alkyl; and

X is C—H or N.

In still another embodiment the present invention provides a compound of formula Ia wherein $R^3$ is $C(CH_3)_3$;

$R^{14}$ is hydrogen, Cl, $CF_3$, $OCF_3$ or $OCHF_2$;

$R^{15}$ is hydrogen, F, Cl or $CH_3$;

$R^{16}$ is hydrogen or F;

$R^{17}$ is hydrogen, halogen, $CH_3$, $CF_3$, Cl or $C(O)OCH_3$;

$R^{18}$ is hydrogen, F or $CH_3$; and

X is C—H or N.

In still another embodiment the present invention provides a compound of formula Ia wherein $R^3$ is $C(CH_3)_3$;

$R^{14}$ is hydrogen, Cl, $CF_3$, $OCF_3$ or $OCHF_2$;

$R^{15}$ is hydrogen, F, Cl or $CH_3$;

$R^{16}$ is hydrogen or F;

$R^{17}$ is hydrogen, halogen, $CH_3$, $CF_3$, Cl or $C(O)OCH_3$;

$R^{18}$ is hydrogen, F or $CH_3$; and

X is C—H.

In still another embodiment the present invention provides a compound of formula Ia wherein $R^3$ is $C(CH_3)_3$;

$R^{14}$ is Cl or $CF_3$;

$R^{15}$ is hydrogen or Cl;

$R^{16}$ is hydrogen or F;

$R^{17}$ and $R^{18}$ are hydrogen; and

X is N.

In another embodiment the present invention provides a compound of formula I as illustrated in formula Ib (Ib)

wherein $R^3$ is $C_1$-$C_6$alkyl;

$R^{14}$, $R^{15}$ and $R^{16}$ are independently hydrogen, halogen, $C_1$-$C_6$alkyl, halogen-$C_1$-$C_6$alkyl or halogen-$C_1$-$C_6$alkoxy;

$R^{17}$ and $R^{18}$ are independently hydrogen, halogen, $C_1$-$C_6$alkyl, halogen-$C_1$-$C_6$alkyl or $C(O)OCH_3$;

X is C—H or N; and

Y is O, N—H, or $N(C_1$-$C_6$alkyl).

In another embodiment the present invention provides a compound of formula I as illustrated in formula Ic (Ic)

wherein $R^3$ is $C_1$-$C_6$alkyl;

$R^{17}$ and $R^{18}$ are independently hydrogen, halogen, $C_1$-$C_6$alkyl, halogen-$C_1$-$C_6$alkyl or $C(O)OCH_3$;

$R^{19}$ is $C_1$-$C_6$alkyl, O—$C_1$-$C_6$alkyl, N(H)—$C_1$-$C_6$alkyl or $N(C_1$-$C_6$alkyl)-$C_1$-$C_6$alkyl; and X is CH or N.

In one embodiment the present invention provides a compound of formula I selected from 1H-pyrrolo[2,3-c]pyridine-7-carboxylic acid (4-tert-butyl-benzyl)-[2-(4-fluoro-3-trifluoromethyl-phenyl)-ethyl]-amide, 1H-pyrrolo[2,3-c]pyridine-7-carboxylic acid (4-tert-butyl-benzyl)-[2-(3-trifluoromethyl-phenyl)-ethyl]-amide, 1H-pyrrolo[2,3-c]pyridine-7-carboxylic acid (4-tert-butyl-benzyl)-[2-(3,4-dichloro-phenyl)-ethyl]-amide, 1H-pyrrolo[2,3-c]pyridine-7-carboxylic acid (4-tert-butyl-benzyl)-[2-(4-fluoro-phenyl)-ethyl]-amide, 1H-pyrrolo[2,3-c]pyridine-7-carboxylic acid (4-tert-butyl-benzyl)-(2-p-tolyl-ethyl)-amide, 1H-pyrrolo[2,3-c]pyridine-7-carboxylic acid (4-tert-butyl-benzyl)-[2-(3-trifluoromethoxy-phenyl)-ethyl]-amide, 1H-pyrrolo[2,3-c]pyridine-7-carboxylic acid (4-tert-butyl-benzyl)-[2-(3-chloro-4-fluoro-phenyl)-ethyl]-amide, 1H-pyrrolo[2,3-c]pyridine-7-carboxylic acid (4-tert-butyl-benzyl)-[2-(4-chloro-3-trifluoromethyl-phenyl)-ethyl]-amide, 1H-pyrrolo[2,3-c]pyridine-7-carboxylic acid (4-tert-butyl-benzyl)-[2-(3-fluoro-5-trifluoromethyl-phenyl)-ethyl]-amide, 1H-pyrrolo[2,3-c]pyridine-7-carboxylic acid (4-tert-butyl-benzyl)-phenethyl-amide, 5-methyl-1H-pyrrolo[2,3-c]pyridine-7-carboxylic acid (4-tert-butyl-benzyl)-[2-(4-fluoro-phenyl)-ethyl]-amide, 5-methyl-1H-pyrrolo[2,3-c]pyridine-7-carboxylic acid (4-tert-butyl-benzyl)-(2-p-tolyl-ethyl)-amide, 5-methyl-1H-pyrrolo[2,3-c]pyridine-7-carboxylic acid (4-tert-butyl-benzyl)-[2-(3-trifluoromethoxy-phenyl)-ethyl]-amide, 5-methyl-1H-pyrrolo[2,3-c]pyridine-7-carboxylic acid (4-tert-butyl-benzyl)-[2-(4-chloro-3-trifluoromethyl-phenyl)-ethyl]-amide, 1H-pyrrolo[2,3-c]pyridine-7-carboxylic acid (4-tert-butyl-benzyl)-[2-(3-difluoromethoxy-phenyl)-ethyl]-amide, 5-methyl-1H-pyrrolo[2,3-c]pyridine-7-carboxylic acid (4-tert-butyl-benzyl)-[2-(3-chloro-4-fluoro-phenyl)-ethyl]-amide, 5-methyl-1H-pyrrolo[2,3-c]pyridine-7-carboxylic acid (4-tert-butyl-benzyl)-[2-(3-fluoro-5-trifluoromethyl-phenyl)-ethyl]-amide, 5-methyl-1H-pyrrolo[2,3-c]pyridine-7-carboxylic acid (4-tert-butyl-benzyl)-phenethyl-amide, 5-methyl-1H-pyrrolo[2,3-c]pyridine-7-carboxylic acid (4-tert-butyl-benzyl)-[2-(3-difluoromethoxy-phenyl)-ethyl]-amide, 5-methyl-1H-pyrrolo[2,3-c]pyridine-7-carboxylic acid (4-tert-butyl-benzyl)-[2-(4-fluoro-3-trifluoromethyl-phenyl)-ethyl]-amide, 5-methyl-1H-pyrrolo[2,3-c]pyridine-7-carboxylic acid (4-tert-butyl-benzyl)-[2-(3-trifluoromethyl-phenyl)-ethyl]-amide, 4-fluoro-1H-pyrrolo[2,3-c]pyridine-7-carboxylic acid (4-tert-butyl-benzyl)-[2-(4-chloro-3-trifluoromethyl-phenyl)-ethyl]-amide, 5-trifluoromethyl-1H-pyrrolo[2,3-c]pyridine-7-carboxylic acid (4-tert-butyl-benzyl)-[2-(4-chloro-3-trifluoromethyl-phenyl)-ethyl]-amide, 4-fluoro-1H-pyrrolo[2,3-c]pyridine-7-carboxylic acid (4-tert-butyl-benzyl)-[2-(4-fluoro-3-trifluoromethyl-phenyl)-ethyl]-amide, 4-fluoro-1H-pyrrolo[2,3-c]pyridine-7-carboxylic acid (4-tert-butyl-benzyl)-[2-(3-trifluoromethyl-phenyl)-ethyl]-amide, 4-fluoro-1H-pyrrolo[2,3-c]pyridine-7-carboxylic acid (4-tert-butyl-benzyl) [2-(3,4-dichloro-phenyl)-ethyl]-amide, 4-fluoro-1H-pyrrolo[2,3-c]pyridine-7-carboxylic acid (4-tert-butyl-benzyl)-[2-(3-trifluoromethoxy-phenyl)-ethyl]-amide, 4-fluoro-1H-pyrrolo[2,3-c]pyridine-7-carboxylic acid (4-tert-butyl-benzyl)-(2-p-tolyl-ethyl)-amide, 5-trifluoromethyl-1H-pyrrolo[2,3-c]pyridine-7-carboxylic acid (4-tert-butyl-benzyl)-[2-(4-fluoro-3-trifluoromethyl-phenyl)-ethyl]-amide, 5-trifluoromethyl-1H-pyrrolo[2,3-c]pyridine-7-carboxylic acid (4-tert-butyl-benzyl)-[2-(3-trifluoromethyl-phenyl)-ethyl]-amide, 5-trifluoromethyl-1H-pyrrolo[2,3-c]pyridine-7-carboxylic acid (4-tert-butyl-benzyl)-[2-(3,4-dichloro-phenyl)-ethyl]-amide, 5-trifluoromethyl-1H-pyrrolo[2,3-c]pyridine-7-carboxylic acid (4-tert-butyl-benzyl)-[2-(3-trifluoromethoxy-phenyl)-ethyl]-amide, 5-trifluoromethyl-1H-pyrrolo[2,3-c]pyridine-7-carboxylic acid (4-tert-butyl-benzyl)-(2-p-tolyl-ethyl)-amide, 4-methyl-1H-pyrrolo[2,3-c]pyridine-7-carboxylic acid (4-tert-butyl-benzyl)-[2-(3,4-dichloro-phenyl)-ethyl]-amide, 5-methyl-1H-pyrrolo[2,3-c]pyridine-7-carboxylic acid (4-tert-butyl-benzyl)-[2-(3,4-dichloro-phenyl)-ethyl]-amide, 4-fluoro-1H-pyrrolo[2,3-c]pyridine-7-carboxylic acid (4-tert-butyl-benzyl)-[2-(4-fluoro-phenyl)-ethyl]-amide, 1H-pyrazolo[3,4-c]pyridine-7-carboxylic acid (4-tert-butyl-benzyl)-[2-(3,4-dichloro-phenyl)-ethyl]-amide, 1H-pyrazolo[3,4-c]pyridine-7-carboxylic acid (4-tert-butyl-benzyl)-[2-(4-chloro-3-trifluoromethyl-phenyl)-ethyl]-amide, 1H-pyrazolo[3,4-c]pyridine-7-carboxylic acid (4-tert-butyl-benzyl)-[2-(3-trifluoromethyl-phenyl)-ethyl]-amide, 5-chloro-1H-pyrrolo[2,3-c]pyridine-7-carboxylic acid (4-tert-butyl-benzyl)-[2-(3,4-dichloro-phenyl)-ethyl]-amide, 5-chloro-1H-pyrrolo[2,3-c]pyridine-7-carboxylic acid (4-tert-butyl-benzyl)-[2-(4-fluoro-phenyl)-ethyl]-amide, 5-chloro-1H-pyrrolo[2,3-c]pyridine-7-carboxylic acid (4-tert-butyl-benzyl)-[2-(3-trifluoromethoxy-phenyl)-ethyl]-amide, 5-chloro-1H-pyrrolo[2,3-c]pyridine-7-carboxylic acid (4-tert-butyl-benzyl)-[2-(3-trifluoromethyl-phenyl)-ethyl]-amide, 7-{(4-tert-butyl-benzyl)-[2-(3,4-dichloro-phenyl)-ethyl]-carbamoyl}-1H-pyrrolo[2,3-c]pyridine-5-carboxylic acid methyl ester, 5-methyl-1H-pyrrolo[2,3-c]pyridine-7-carboxylic acid (4-tert-butyl-benzyl)-{2-[(4-chloro-phenyl)-methyl-amino]-ethyl}-amide, and 5-methyl-1H-pyrrolo[2,3-c]pyridine-7-carboxylic acid butyl-(4-tert-butyl-benzyl)-amide.

In addition to the foregoing the present invention also provides a process for the production of a compound of formula I which process comprises reacting a carboxylic acid derivative of formula II

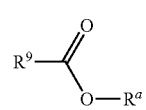

(II)

wherein $R^a$ is hydrogen or $C_1$-$C_6$alkyl, and $R^9$ has the above meanings, with a secondary amine of formula III

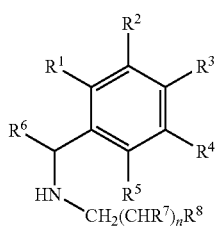
(III)

wherein $R^1$, $R^2$, $R^3$, $R^4$, $R^5$, $R^6$, $R^7$, $R^8$ and n have the above meanings.

In the case where acids ($R^a$=H) of formula II are used in this process, standard peptide coupling reagents can be applied to activate the acid prior to the coupling reaction. Typically, the acid derivative II ($R^a$=H) is mixed with a coupling reagent such as 1-ethyl-3-(3-dimethylaminopropyl)-carbodiimide or its hydrochloride, N,N'-dicyclohexylcarbodiimide or N,N,N',N'-tetramethyl-O-(benzotriazol-1-yl)uronium hexafluorophosphate in an inert solvent such as N,N-dimethylformamide, N,N-dimethylacetamide or dichloromethane together with the appropriate secondary amine derivative III, optionally in the presence of a base (e.g. diisopropylethylamine, triethylamine, 4-methylmorpholine) and/or 1-hydroxybenzotriazole. The reaction mixture is stirred for 1 to 72 hours at a temperature between −30° C. and 70° C. (e.g. ambient temperature).

Acids ($R^a$=H) of formula II can be produced from esters of formula II ($R^a$=$C_1$-$C_6$alkyl) by alkaline hydrolysis using a base such as sodium hydroxide or potassium hydroxide in a suitable solvent, e.g., water, tetrahydrofuran, methanol, ethanol, or mixtures thereof, at 0-100° C. and subsequent acidification of the sodium or potassium carboxylates, using a mineral acid such as hydrochloric acid or sulfuric acid.

Alternatively, esters of formula II ($R^a$=$C_1$-$C_6$alkyl) are subjected to alkaline hydrolysis as described above, to produce the sodium or potassium carboxylates, respectively, which are directly reacted with appropriate secondary amines III, using one of the peptide coupling methods described above.

Alternatively, esters of formula II ($R^a$=$C_1$-$C_6$alkyl) may be directly used in the coupling process. In that case, the amine derivative III is treated with trimethylaluminum in an inert solvent such as dichloromethane or toluene at ambient temperature prior to the addition of the ester derivative II.

Esters of formula II ($R^a$=$C_1$-$C_6$alkyl) are prepared from halides of formula IV $R^9$-Hal  (IV)

wherein Hal is halogen, e.g. Cl or Br, and $R^9$ has the above meanings, using methods well known in the art, e.g., palladium-catalyzed carbonylation. The reaction is typically carried out in an alcoholic solvent such as methanol or ethanol, or in a mixture of an alcoholic solvent with an aprotic solvent, like toluene or ethyl acetate, at temperatures between 25° C. and 150° C. under an atmosphere of carbon monoxide at pressures between 1 bar and 100 bar, and in the presence of a base, e.g., triethylamine or 4-methylmorpholine. Typically used palladium catalysts are palladium dichloride, tetrakis(triphenylphosphine)palladium(0) or dichloro[1,1'-bis(diphenylphosphino)ferrocene]palladium.

Halides of formula IV can be represented by IVa (7-halo-1H-pyrrolo[2,3-c]pyridines) or IVb (7-halo-1H-pyrazolo[3,4-c]pyridines):

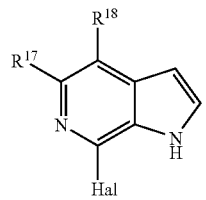
(IVa)

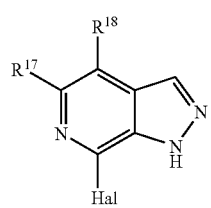
(IVb)

wherein Hal is halogen, e.g. Cl or Br, and $R^{17}$ and $R^{18}$ have the above meanings.

7-Halo-1H-pyrrolo[2,3-c]pyridines of formula IVa can be synthesized by reaction of 2-halo-3-nitropyridines of formula V

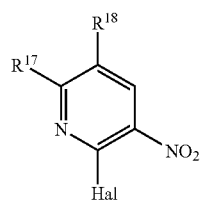
(V)

wherein Hal is halogen, e.g. Cl or Br, and $R^{17}$ and $R^{18}$ have the above meanings, with three equivalents of vinylmagnesium bromide in a solvent such as tetrahydrofuran, at a temperature between −78° C. and 0° C. 2-halo-3-nitropyridines are either commercially available or can be synthesized using methods known in the art, e.g., halogenation of 3-nitropyridine-2-ones with a reagents such as phosphorus oxychloride, phosphorus pentachloride, or phosphorus oxybromide.

Alternatively, compounds of formula IVa can be synthesized from 3-aminopyridines of formula VI as outlined in scheme 1.

Scheme 1

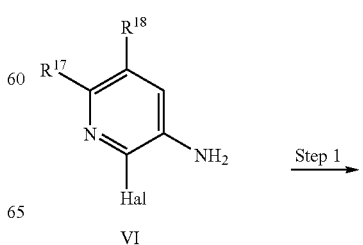
VI

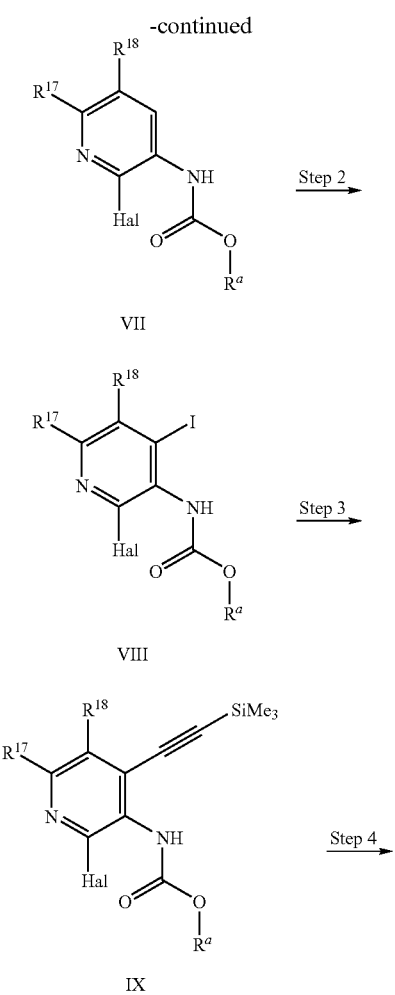

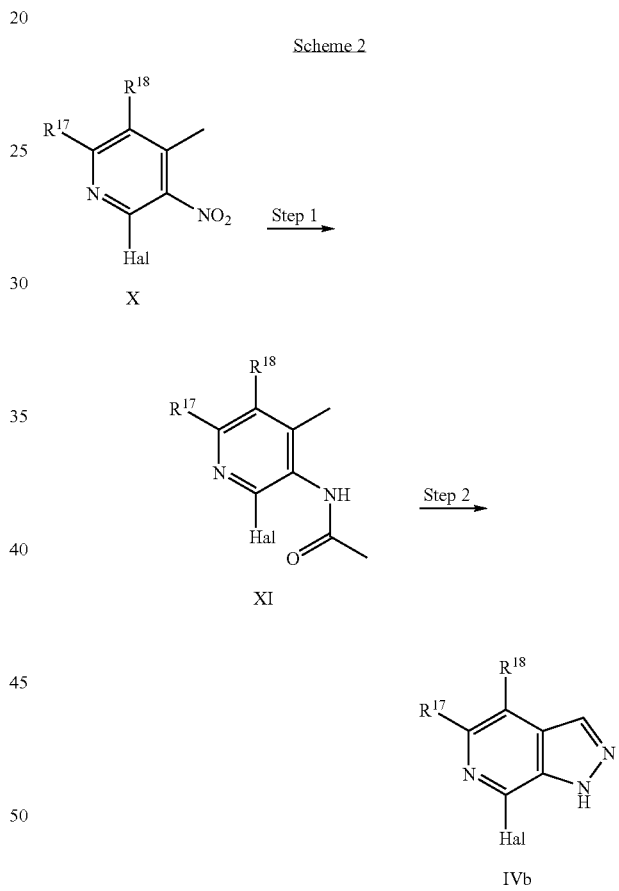

In step 3, scheme 1, 4-iodopyridine VIII is coupled with trimethylsilylacetylene using methods well known in the art, e.g., Sonogashira reaction, leading to 4-alkynylpyridine IX. The reaction is carried out in the presence of a suitable catalyst system such as bis-(triphenylphosphine)palladium(II) dichloride and copper(I) iodide, in a liquid amine as solvent, e.g., triethylamine or diisopropylethylamine, optionally in the presence of a co-solvent such as tetrahydrofuran or 1,4-dioxane, at a temperature between 0° C. and 80° C.

In step 4, scheme 1, 4-alkynylpyridine IX is converted to 1H-pyrrolo[2,3-c]pyridine IVa using methods known in the art. This reaction takes place in the presence of a suitable reagent, e.g., tetrabutylammonium fluoride, in a solvent such as tetrahydrofuran, at a temperature between 0° C. and 60° C.

7-Halo-1H-pyrazolo[3,4-c]pyridines of general formula IVb can be synthesized from 2-halo-3-nitro-4-methylpyridines X as outlined in scheme 2:

In step 1, scheme 1, 3-aminopyridine VI is converted into alkylcarbamate VII ($R^a$=methyl or ethyl) by reaction with an appropriate reagent, e.g., methyl chloroformate or ethyl chloroformate. The reaction is carried out in an inert solvent such as dichloromethane or tetrahydrofuran, in the presence of a base, e.g., pyridine, triethylamine, or sodium hydride, at a temperature between −20° C. and the boiling point of the solvent.

In step 2, scheme 1, alkylcarbamate VII is iodinated at the free ortho position to produce 4-iodopyridine VIII. This conversion is accomplished by treatment of VII with two equivalents of a suitable base, e.g., sec-butyllithium, optionally in the presence of N,N,N',N'-tetramethylethylenediamine, and reaction of the dianion intermediate with an electrophilic iodine source, e.g., elemental iodine. Suitable solvents are e.g., tetrahydrofuran or diethyl ether. The reaction temperature may e.g. be below 0° C.

In step 1, scheme 2, 3-nitropyridine X is converted to the 3-acetamidopyridine analogue XI using methods known in the art, i.e., nitro reduction and subsequent acetylation. The reduction of the nitro group is performed using reducing metals such as iron, tin or tin(II) chloride, in a solvent such as diethyl ether, acetic acid, water, methanol, or mixtures thereof, optionally in the presence of an acid such as hydrochloric acid or ammonium chloride, at a temperature between 20° C. and the boiling point of the solvent. The acetylation of the 3-aminopyridine intermediate is carried out using a suitable acetylation reagent, e.g. acetic anhydride, optionally in the presence of a co-solvent such as toluene or dichloromethane, at a temperature between 0° C. and 50° C.

In step 2, scheme 2, 3-acetamidopyridine XI is elaborated to the 1H-pyrazolo[3,4-c]pyridine IVb using a reaction sequence well known in the art, e.g, nitrosative cyclization and subsequent deacetylation. The nitrosative cyclization is performed using a suitable nitrosating agent, e.g, isoamyl nitrite or sodium nitrite, in the presence of acetic anhydride and a base such as potassium acetate, in a solvent such as benzene, to afford a mixture of acetylated 1H-pyrazolo[3,4-c]pyridines. This mixture is hydrolyzed with aqueous sodium or potassium hydroxide, at a temperature between 20° C. and 100° C., to afford 1H-pyrazolo[3,4-c]pyridine IVb.

Secondary amines of the general formula III can be synthesized as outlined in scheme 3.

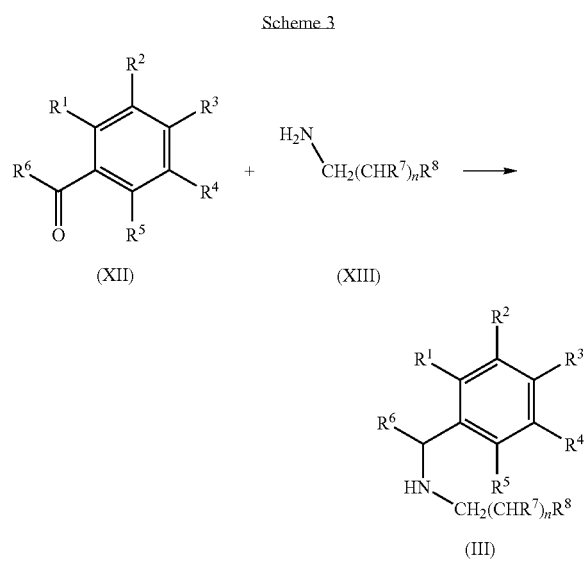

Scheme 3

Compounds III are synthesized using methods well known to the skilled artisan, e.g., by reductive amination of benzaldehyde ($R^6$=H) alkyl-phenyl-ketone ($R^6$=$C_1$-$C_6$alkyl) derivatives XII with amines XIII or their hydrochloride salts. The reaction is performed in a solvent such as methanol, acetic acid, trifluoroacetic acid, tetrahydrofuran, dichloromethane, or mixtures thereof, in the presence of a suitable reducing agent such as sodium borohydride, sodium cyanoborohydride, or sodium triacetoxyborohydride, optionally in the presence of a Lewis acid such as titanium(IV) chloride, at a temperature between 0° C. and the boiling point of the solvent. In the case where hydrochloride salts of XIII are used, a suitable base such as sodium carbonate or potassium carbonate is added to the reaction mixture. The reactants XII and XIII are commercially available or are synthesized using standard methods, e.g., as described in the experimental section.

In general, the nomenclature used in this application is based on AUTONOM™-v.4.0, a Beilstein Institute computerized system for the generation of IUPAC systematic nomenclature.

The following abbreviations are used: RT: room temperature; HBTU: N,N,N',N'-tetramethyl-O-(benzotriazol-1-yl) uronium hexafluorophosphate; THF: tetrahydrofuran; DMF: N,N-dimethylformamide.

Preparation of the Starting Compounds

EXAMPLE H1

Preparation of 2-(4-fluoro-3-trifluoromethyl-phenyl)-ethylamine hydrochloride

A solution of (4-fluoro-3-trifluoromethyl-phenyl)-acetonitrile (4.00 g, 19.3 mmol) in THF was added dropwise at 0-5° C. to a suspension of lithium aluminum hydride (1.61 g, 42.4 mmol) in diethyl ether (20 mL). The ice bath was removed and the reaction mixture was allowed to reach RT, then heated at reflux overnight. After cooling to 0° C., saturated aq. sodium sulfate solution was carefully added. After the initial exothermic reaction had subsided, the flask was allowed to warm to ambient temperature and solid magnesium sulfate (dry) was added to dry the suspension, which was subsequently filtered and washed with diethyl ether. After removal of the solvent, the residue was dissolved in diethyl ether (50 mL), treated with hydrogen chloride solution (2.6 M in diethyl ether, 8 mL), and evaporated to dryness, leading to a solid orange foam. This residue was dissolved in dichloromethane (200 mL), and treated with water (100 mL), followed by 1 M aq. hydrochloric acid solution (50 mL), and stirred for 15 minutes, then the organic layer was separated and extracted a second time with 1 M aq. hydrochloric acid solution (50 mL). The combined aqueous phases were then washed with dichloromethane (50 mL), treated with concentrated aq. sodium hydroxide solution to adjust the pH to 12, and extracted twice with dichloromethane. The combined organic phases were washed with water and dried over magnesium sulfate. After filtration and evaporation of the solvent, the residue was dissolved in diethyl ether (5 mL), treated with hydrogen chloride solution (2.6 M in diethyl ether, 2 mL), and stirred for 10 min. The precipitate was collected by filtration and dried to afford the title compound (632 mg, 13%). White solid, MS (ISP) 208.2 (M−Cl)$^+$.

EXAMPLE H2

Preparation of 2-(3-chloro-4-fluoro-phenyl)-ethylamine hydrochloride (H2.1)

Borane-tetrahydrofuran complex solution (1 M in THF, 132 mL, 132 mmol) was added dropwise over 30 min at 0-5° C. to a solution of 3-chloro-4-fluoro-phenylacetonitrile (4.37 g, 25.8 mmol) in THF (40 mL), then the reaction mixture was stirred at RT for 20 min and refluxed for 21 h. The reaction mixture was then cooled to 0° C., and methanol (30 mL) was added at 2-5° C. over 45 minutes. After refluxing for 1 h the reaction mixture was concentrated, the residue dissolved in dichloromethane and the amine extracted twice with 1 M aq. hydrochloric acid solution. The combined aqueous phases were then treated with concentrated aq. sodium hydroxide solution to adjust the pH to 12, then extracted twice with dichloromethane. The combined organic phases were washed with water, dried over magnesium sulfate, filtered and concentrated, leading to a colorless oil (4.3 g). This was dissolved in diethyl ether (125 mL), treated with hydrogen chloride solution (2.6 M in diethyl ether), and stirred at RT for 1 h. The precipitate was then collected by filtration to afford the title compound (3.93 g, 73%) White solid, MS (ISP) 174.1 (M−Cl)$^+$.

In analogy to the above procedure the following compounds were prepared:

| no. | compound of formula XIII | starting material | MS (ISP) (M − Cl)+ |
|---|---|---|---|
| H2.2 | 2-(3-trifluoromethoxy-phenyl)-ethylamine hydrochloride | (3-trifluoromethoxy-phenyl)-acetonitrile | 206.2 |
| H2.3 | 2-(3-fluoro-5-trifluoromethyl-phenyl)-ethylamine hydrochloride | (3-fluoro-5-trifluoromethyl-phenyl)-acetonitrile | 207.1 |
| H2.4 | 2-(3-trifluoromethoxy-phenyl)-ethylamine hydrochloride | (3-difluoromethoxy-phenyl)-acetonitrile | 188.3 |

EXAMPLE H3

Preparation of 2-(4-chloro-3-trifluoromethyl-phenyl)-ethylamine hydrochloride

A mixture of 4-bromomethyl-1-chloro-2-trifluoromethyl-benzene (3.94 g, 14.4 mmol) and sodium cyanide (1.06 g, 21.6 mmol) in dimethyl sulfoxide (12 mL) was heated at 50° C. for one hour. The reaction mixture was then poured on ice water and extracted four times with dichloromethane. The combined organic phases were washed with water, dried over magnesium sulfate, filtered and concentrated, leading to (4-chloro-3-trifluoromethyl-phenyl)-acetonitrile (3.19 g, 14.4 mmol) as a dark red oil. This crude material was transformed into the title compound in accordance with the general method of example H2. White solid, MS (ISP) 224.1 (M−Cl)+.

EXAMPLE A1

Preparation of (4-tert-butyl-benzyl)-[2-(4-fluoro-3-trifluoromethyl-phenyl)-ethyl]-amine (A1.1)

A mixture of 4-tert-butylbenzaldehyde (0.62 mL, 3.69 mmol), 2-(4-fluoro-3-trifluoromethyl-phenyl)-ethylamine hydrochloride (600 mg, 2.46 mmol), and potassium carbonate (340 mg, 2.46 mmol) in methanol (7 mL) was stirred for 30 min at RT and subsequently refluxed for 2 h. After cooling to RT, sodium borohydride (140 mg, 3.69 mmol) was added and reaction mixture was refluxed for 3 h. After cooling, the reaction mixture was treated with 1 M aq. hydrochloric acid solution (0.5 M) at RT and concentrated. The residue was partitioned between water and ethyl acetate. After separation of the organic phase, the aqueous phase was extracted with ethyl acetate and the combined organic phases were washed with brine, dried with magnesium sulfate, filtered, and concentrated. The residue was purified by column chromatography (SiO$_2$; ethyl acetate/heptane 1:4 then 1:2) to afford the title compound (784 mg, 90%). Light yellow oil, MS (ISP) 354.3 (M+H)+.

In analogy to the above procedure the following compounds were prepared

| No. | compound of formula III | compound of formula XIII (starting material) | MS (ISP) (M + H)+ |
|---|---|---|---|
| A1.2 | (4-tert-butyl-benzyl)-[2-(3-trifluoromethoxy-phenyl)-ethyl]-amine | 2-(3-trifluoromethoxy-phenyl)-ethylamine hydrochloride | 352.3 |
| A1.3 | (4-tert-butyl-benzyl)-[2-(3-chloro-4-fluoro-phenyl)-ethyl]-amine | 2-(3-chloro-4-fluoro-phenyl)-ethylamine hydrochloride | 320.3 |
| A1.4 | (4-tert-butyl-benzyl)-[2-(4-chloro-3-trifluoromethyl-phenyl)-ethyl]-amine | 2-(4-chloro-3-trifluoromethyl-phenyl)-ethylamine hydrochloride | 370.2 |
| A1.5 | (4-tert-butyl-benzyl)-[2-(3-fluoro-5-trifluoromethyl-phenyl)-ethyl]-amine | 2-(3-fluoro-5-trifluoromethyl-phenyl)-ethylamine hydrochloride | 354.3 |
| A1.6 | (4-tert-butyl-benzyl)-[2-(3-difluoromethoxy-phenyl)-ethyl]-amine | 2-(3-trifluoromethoxy-phenyl)-ethylamine hydrochloride | 334.3 |

EXAMPLE A2

Preparation of (4-tert-butyl-benzyl)-[2-(3-trifluoromethyl-phenyl)-ethyl]-amine (A2.1)

A solution of 4-tert-butylbenzaldehyde (0.38 mL, 2.25 mmol) and 2-(3-trifluoromethyl-phenyl)-ethylamine (0.24 mL, 1.50 mmol) in methanol (4.5 mL) was stirred for 30 min at RT and subsequently refluxed for 4 h. After cooling, sodium borohydride (85 mg, 2.25 mmol) was added at RT, then after stirring for 5 min the reaction mixture was refluxed for 4 h. After cooling down to RT, the reaction mixture was treated with 1 M aq. hydrochloric acid solution (4 drops) and concentrated. The residue was dissolved in water/ethyl acetate. After separation of the organic phase, the aqueous phase was extracted with ethyl acetate, the combined organic phases were washed with brine, dried with magnesium sulfate, filtered, and concentrated. The residue was purified by column chromatography (SiO$_2$; ethyl acetate/heptane 1:2) to afford the title compound (450 mg, 89%). Colorless viscous oil, MS (ISP) 336.3 (M+H)+.

In analogy with the above procedure the following compounds were prepared

4:1) afforded the title compound (4.47 g, 70%). White solid, MS (EI) 219.1 (100), 254.1 (28, M$^+$).

| No. | compound of formula III | compound of formula XIII (starting material) | MS (ISP) (M + H)$^+$ |
|---|---|---|---|
| A2.2 | (4-tert-butyl-benzyl)-[2-(4-fluoro-phenyl)-ethyl]-amine | 2-(4-fluoro-phenyl)-ethylamine | 286.2 |
| A2.3 | (4-tert-butyl-benzyl)-[2-(3,4-dichloro-phenyl)-ethyl]-amine | 2-(3,4-dichloro-phenyl)-ethylamine | 336.2 |
| A2.4 | (4-tert-butyl-benzyl)-(2-p-tolyl-ethyl)-amine | 2-p-tolyl-ethylamine | 282.2 |
| A2.5 | (4-tert-butyl-benzyl)-phenethyl-amine | phenethylamine | 268.3 |
| A2.6 | N'-(4-tert-butyl-benzyl)-N-(4-chloro-phenyl)-N-methyl-ethane-1,2-diamine | N-(4-chloro-phenyl)-N-methyl-ethane-1,2-diamine | 331.2 |
| A2.7 | butyl-(4-tert-butyl-benzyl)-amine | butylamine | 220.4 |

EXAMPLE P1

Preparation of
7-chloro-5-methyl-1H-pyrrolo[2,3-c]pyridine (P1.1)

Vinylmagnesium bromide solution (1 M in THF, 111 mL, 111 mmol) was added dropwise at −78° C. to a solution of 2-chloro-3-nitro-6-picoline (6.19 g, 35.2 mmol) in THF (200 mL). The dry ice cooling bath was replaced by an ice/NaCl cooling bath, and the reaction mixture was allowed to reach RT over 18 h, then the reaction mixture was carefully treated with 20% aq. ammonium chloride solution (210 mL). The reaction mixture was extracted with ethyl acetate, the organic layer was dried (MgSO$_4$), and evaporated. Chromatography of the residue (SiO$_2$, heptane/ethyl acetate gradient) afforded the title compound (2.58 g, 44%). Orange solid, MS (EI) 166.1 (100, M$^+$).

In analogy with the above procedure the following compounds were prepared:

b) (2-Chloro-4-iodo-6-trifluoromethyl-pyridin-3-yl)-carbamic acid methyl ester: sec-Butyllithium solution (1.3 M in cyclohexane, 7.55 mL, 5.81 mmol) was added at −78° C. to a solution of (2-chloro-6-trifluoromethyl-pyridin-3-yl)-carbamic acid methyl ester (1.00 g, 3.93 mmol) and N,N,N',N'-tetramethylethylenediamine (1.14 g, 9.82 mmol) in THF (50 mL). The solution was stirred for 1 h at −10° C., then cooled again to −78° C. and treated with a solution of iodine (1.66 g, 6.52 mmol) in THF (20 mL). After stirring for 1 h at −10° C., the reaction mixture was partitioned between ethyl acetate and 30% aq. sodium sulfite solution. The organic layer was washed with brine, dried (MgSO$_4$), and evaporated. Chromatography of the residue (SiO$_2$, dichloromethane) afforded the title compound (810 mg, 54%). White solid, MS (EI) 345.0 (100), 379.9 (2, M$^+$).

c) 7-Chloro-5-trifluoromethyl-1H-pyrrolo[2,3-c]pyridine: A solution of bis-(triphenylphosphine)palladium(II) dichloride (52 mg, 74 μmol) and copper(I) iodide (14 mg, 74 μmol)

| No. | compound of formula IVa | compound of formula V (starting material) | MS |
|---|---|---|---|
| P1.2 | 7-chloro-4-methyl-1H-pyrrolo[2,3-c]pyridine | 2-chloro-5-methyl-3-nitropyridine | MS (EI) 166.1 (100, M$^+$) |
| P1.3 | 7-bromo-5-chloro-1H-pyrrolo[2,3-c]pyridine | 2-bromo-6-chloro-3-nitro-pyridine | MS (ISP) 231.0/ 233.0 (M + H)$^+$ |

EXAMPLE P2

Preparation of 7-chloro-5-trifluoromethyl-1H-pyrrolo[2,3-c]pyridine a) (2-Chloro-6-trifluoromethyl-pyridin-3-yl)-carbamic acid methyl ester: Pyridine (3.98 g, 50.4 mmol) and methyl chloroformate (2.62 g, 27.7 mmol) were added at 0° C. to a solution of 3-amino-2-chloro-6-trifluoromethylpyridine (4.95 g, 25.2 mmol) in dichloromethane (100 ml). The reaction mixture was stirred for 18 h at RT, then cooled to 0° C. and treated with pyridine (3.98 g, 50.4 mmol) and methyl chloroformate (0.95 g, 10 mmol). The reaction mixture was stirred for 24 h at RT and 2.5 h at reflux, then partitioned between ethyl acetate and 10% aq. sodium hydrogencarbonate solution. The organic layer was washed with 10% aq. citric acid solution and brine, dried (MgSO$_4$), and evaporated. Chromatography of the residue (SiO$_2$, heptane/ethyl acetate in triethylamine (42 mL) was purged with argon for 10 min and heated at reflux for 20 min. After cooling to 0° C. (2-chloro-4-iodo-6-trifluoromethyl-pyridin-3-yl)-carbamic acid methyl ester (2.83 g, 7.44 mmol) and trimethylsilylacetylene (877 mg, 8.93 mmol) were added. The reaction mixture was allowed to reach RT over 1 h and heated at 40° C. for 1 h, then partitioned between ethyl acetate and half-saturated aq. ammonium chloride solution. The organic layer was washed with brine, dried (MgSO$_4$), and evaporated. The residue was dissolved in THF (50 mL) and treated with tetrabutylammonium fluoride solution (1 M in THF, 14.9 mL, 14.9 mmol) at 0° C. The reaction mixture was allowed to reach RT over 1 h and heated at 40° C. for 30 min, then partitioned between ethyl acetate and water. The organic layer was washed with brine, dried (MgSO$_4$), and evaporated. Chromatography of the residue (SiO$_2$, heptane/ethyl acetate 4:1) afforded the title compound (1.13 g, 65%). Light yellow solid, MS (EI) 220.1 (100, M$^+$).

EXAMPLE P3

Preparation of 2-bromo-6-chloro-3-nitro-pyridine tert-Butyl nitrite (990 mg, 9.60 mmol) was added portion-wise at 65° C. under a nitrogen atmosphere to a stirred suspension of 2-amino-6-chloro-3-nitropyridine (1.00 g, 5.76 mmol) and copper(II) bromide (1.56 g, 6.91 mmol) in acetonitrile (25 mL), and stirring was continued for 30 min. After cooling, the reaction mixture was partitioned between ethyl acetate and 2 M aq. hydrochloric acid solution. The organic layer was dried (MgSO$_4$), and evaporated. Chromatography of the residue (SiO$_2$, heptane-dichloromethane gradient) afforded the title compound (1.11 g, 81%). Yellow solid, MS (EI) 235.9/237.9 (78/100, M$^+$).

EXAMPLE E1

Preparation of 1H-pyrrolo[2,3-c]pyridine-7-carboxylic acid methyl ester (E1.1)

A solution of 7-chloro-1H-pyrrolo[2,3-c]pyridine (*J. Org. Chem.* 2002, 67, 2345; 200 mg, 1.31 mmol), triethylamine (549 mg, 5.43 mmol), and 1,1'-bis(diphenylphosphino)ferrocene-palladium(II)dichloride dichloromethane complex (54 mg, 66 μmol) in methanol (3 mL) and toluene (3 mL) was stirred for 17 h at 110° C. under a carbon monoxide atmosphere (50 bar). After cooling and evaporation of volatile material, the residue was chromatographed (SiO$_2$, heptane/ethyl acetate gradient), to afford the title compound (194 mg, 84%). Off-white solid, MS (EI) 118.1 (100), 146.1 (26), 176.2 (35, M$^+$).

In analogy with the above procedure the following compounds were prepared:

EXAMPLE C1

Preparation of 1H-pyrrolo[2,3-c]pyridine-7-carboxylic acid

1H-Pyrrolo[2,3-c]pyridine-7-carboxylic acid methyl ester (example E1, 50 mg, 0.28 mmol) was dissolved in THF (0.57 mL) and treated with 2 M aq. potassium hydroxide solution (0.57 mL, 1.1 mmol), then after 1 h acidified with 2M aq. hydrochloric acid solution and extracted with dichloromethane. The aqueous layer was evaporated and the residue was taken up in methanol and the residue was taken up in methanol and filtered. The filtrate was evaporated to afford the title compound (71 mg), which contained an unspecified amount of potassium chloride. MS (EI) 118.1 (100), 162.1 (53, M$^+$); $^1$H-NMR (300 MHz, CD$_3$OD): 8.30-8.25 (m, 2H), 8.24 (d, J=3.0, 1H), 7.07 (d, J=3.0, 1H).

Preparation of Compounds of Formula I

EXAMPLE B1

1H-Pyrrolo[2,3-c]pyridine-7-carboxylic acid (4-tert-butyl-benzyl)-[2-(4-fluoro-3-trifluoromethyl-phenyl)-ethyl]-amide (B1.1)

Trimethylaluminum solution (2 M in heptane, 0.14 mL, 0.28 mmol) was added at RT to a solution of (4-tert-butyl-benzyl)-[2-(4-fluoro-3-trifluoromethyl-phenyl)-ethyl]-amine (100 mg, 0.28 mmol) in dichloromethane (0.7 mL), then after 15 min a solution of 1H-pyrrolo[2,3-c]pyridine-7-carboxylic acid methyl ester (50 mg, 0.14 mmol) in dichloromethane was added. After 2 h the reaction mixture was partitioned between ethyl acetate and 2 M aq. hydrochloric acid solution. The organic layer was washed with brine, dried (MgSO$_4$), evaporated, and chromatographed (SiO$_2$, heptane/ethyl acetate gradient), to afford the title compound (70 mg, 50%). White foam, MS (ISP) 498.3 (M+H)$^+$.

| No. | compound of formula II | alcohol reagent | starting material of formula IV | |
|---|---|---|---|---|
| E1.2 | 1H-pyrrolo[2,3-c]pyridine-7-carboxylic acid ethyl ester | ethanol | 7-chloro-1H-pyrrolo[2,3-c]pyridine | MS (EI) 118.1 (100), 146.1 (26), 190.1 (15, M$^+$) |
| E1.3 | 1H-pyrrolo[2,3-c]pyridine-7-carboxylic acid propyl ester | 1-propanol | 7-chloro-1H-pyrrolo [2,3-c]pyridine | MS (EI) 118.1 (100), 146.1 (28), 204.1 (9, M$^+$) |
| E1.4 | 5-methyl-1H-pyrrolo[2,3-c]pyridine-7-carboxylic acid ethyl ester | ethanol | 7-chloro-5-methyl-1H-pyrrolo[2,3-c]pyridine | MS (EI) 132.2 (100), 160.1 (18), 204.2 (19) |
| E1.5 | 4-methyl-1H-pyrrolo[2,3-c]pyridine-7-carboxylic acid ethyl ester | ethanol | 7-chloro-4-methyl-1H-pyrrolo[2,3-c]pyridine | MS (ISP) 205.1 (M + H)$^+$ |
| E1.6 | 5-trifluoromethyl-1H-pyrrolo[2,3-c]pyridine-7-carboxylic acid ethyl ester | ethanol | 7-chloro-5-trifluoromethyl-1H-pyrrolo[2,3-c]pyridine | MS (EI) 186.1 (100), 214.1 (15), 258.1 (10, M$^+$) |
| E1.7 | 5-chloro-1H-pyrrolo[2,3-c]pyridine-7-carboxylic acid ethyl ester | ethanol | 7-bromo-5-chloro-1H-pyrrolo[2,3-c]pyridine | MS (EI) 152.0 (100), 180.0 (13), 224.1 (30, M$^+$) |
| E1.8 | 4-fluoro-1H-pyrrolo[2,3-c]pyridine-7-carboxylic acid ethyl ester | ethanol | 7-chloro-4-fluoro-1H-pyrrolo[2,3-c]pyridine* | MS (EI) 136.1 (100), 164.1 (20), 208.2 (20, M$^+$) |
| E1.9 | 1H-pyrazolo[3,4-c]pyridine-7-carboxylic acid ethyl ester | ethanol | 7-chloro-1H-pyrazolo[3,4-c]pyridine** | MS (ISP) 192.3 (M + H)$^+$ |

*U.S. Pat. No. 6,476,034;
**Heterocycles 2002, 57, 2335

In analogy with the above procedure the following compounds were prepared:

| No. | compound of formula I | starting material of formula II | starting material of formula III | MS |
|---|---|---|---|---|
| B1.2 | 1H-pyrrolo[2,3-c]pyridine-7-carboxylic acid (4-tert-butyl-benzyl)-[2-(3-trifluoromethyl-phenyl)-ethyl]-amide | 1H-pyrrolo[2,3-c]pyridine-7-carboxylic acid methyl ester | (4-tert-butyl-benzyl)-[2-(3-trifluoromethyl-phenyl)-ethyl]-amine | MS (ISP) 480.5 (M + H)$^+$ |
| B1.3 | 1H-pyrrolo[2,3-c]pyridine-7-carboxylic acid (4-tert-butyl-benzyl)-[2-(3,4-dichloro-phenyl)-ethyl]-amide | 1H-pyrrolo[2,3-c]pyridine-7-carboxylic acid ethyl ester | (4-tert-butyl-benzyl)-[2-(3,4-dichloro-phenyl)-ethyl]-amine | MS (EI) 334.2 (100, M$^+$) |
| B1.4 | 1H-pyrrolo[2,3-c]pyridine-7-carboxylic acid (4-tert-butyl-benzyl)-[2-(4-fluoro-phenyl)-ethyl]-amide | 1H-pyrrolo[2,3-c]pyridine-7-carboxylic acid methyl ester | (4-tert-butyl-benzyl)-[2-(4-fluoro-phenyl)-ethyl]-amine | MS (EI) 284.3 (100), 429.3 (4, M$^+$) |
| B1.5 | 1H-pyrrolo[2,3-c]pyridine-7-carboxylic acid (4-tert-butyl-benzyl)-(2-p-tolyl-ethyl)-amide | 1H-pyrrolo[2,3-c]pyridine-7-carboxylic acid ethyl ester | (4-tert-butyl-benzyl)-(2-p-tolyl-ethyl)-amine | MS (EI) 280.2 (100), 425.3 (6, M$^+$) |
| B1.6 | 1H-pyrrolo[2,3-c]pyridine-7-carboxylic acid (4-tert-butyl-benzyl)-[2-(3-trifluoromethoxy-phenyl)-ethyl]-amide | 1H-pyrrolo[2,3-c]pyridine-7-carboxylic acid ethyl ester | (4-tert-butyl-benzyl)-[2-(3-trifluoromethoxy-phenyl)-ethyl]-amine | MS (EI) 350.2 (100), 495.3 (5, M$^+$) |
| B1.7 | 1H-pyrrolo[2,3-c]pyridine-7-carboxylic acid (4-tert-butyl-benzyl)-[2-(3-chloro-4-fluoro-phenyl)-ethyl]-amide | 1H-pyrrolo[2,3-c]pyridine-7-carboxylic acid ethyl ester | (4-tert-butyl-benzyl)-[2-(3-chloro-4-fluoro-phenyl)-ethyl]-amine | MS (EI) 318.2 (100), 463.3 (7, M$^+$) |
| B1.8 | 1H-pyrrolo[2,3-c]pyridine-7-carboxylic acid (4-tert-butyl-benzyl)-[2-(4-chloro-3-trifluoromethyl-phenyl)-ethyl]-amide | 1H-pyrrolo[2,3-c]pyridine-7-carboxylic acid propyl ester | (4-tert-butyl-benzyl)-[2-(4-chloro-3-trifluoromethyl-phenyl)-ethyl]-amine | MS (EI) 368.2 (100), 513.4 (5, M$^+$) |
| B1.9 | 1H-pyrrolo[2,3-c]pyridine-7-carboxylic acid (4-tert-butyl-benzyl)-[2-(3-fluoro-5-trifluoromethyl-phenyl)-ethyl]-amide | 1H-pyrrolo[2,3-c]pyridine-7-carboxylic acid propyl ester | (4-tert-butyl-benzyl)-[2-(3-fluoro-5-trifluoromethyl-phenyl)-ethyl]-amine | MS (EI) 352.2 (100), 497.4 (6, M+) |
| B1.10 | 1H-pyrrolo[2,3-c]pyridine-7-carboxylic acid (4-tert-butyl-benzyl)-phenethyl-amide | 1H-pyrrolo[2,3-c]pyridine-7-carboxylic acid propyl ester | (4-tert-butyl-benzyl)-phenethyl-amine | MS (EI) 266.3 (100), 411.3 (5, M+) |
| B1.11 | 5-methyl-1H-pyrrolo[2,3-c]pyridine-7-carboxylic acid (4-tert-butyl-benzyl)-[2-(4-fluoro-phenyl)-ethyl]-amide | 5-methyl-1H-pyrrolo[2,3-c]pyridine-7-carboxylic acid ethyl ester | (4-tert-butyl-benzyl)-[2-(4-fluoro-phenyl)-ethyl]-amine | MS (ISP) 444.4 (M + H)$^+$ |
| B1.12 | 5-methyl-1H-pyrrolo[2,3-c]pyridine-7-carboxylic acid (4-tert-butyl-benzyl)-(2-p-tolyl-ethyl)-amide | 5-methyl-1H-pyrrolo[2,3-c]pyridine-7-carboxylic acid ethyl ester | (4-tert-butyl-benzyl)-(2-p-tolyl-ethyl)-amine | MS (ISP) 440.5 (M + H)$^+$ |
| B1.13 | 5-methyl-1H-pyrrolo[2,3-c]pyridine-7-carboxylic acid (4-tert-butyl-benzyl)-[2-(3-trifluoromethoxy-phenyl)-ethyl]-amide | 5-methyl-1H-pyrrolo[2,3-c]pyridine-7-carboxylic acid ethyl ester | (4-tert-butyl-benzyl)-[2-(3-trifluoromethoxy-phenyl)-ethyl]-amine | MS (ISP) 510.6 (M + H)$^+$ |
| B1.14 | 5-methyl-1H-pyrrolo[2,3-c]pyridine-7-carboxylic acid (4-tert-butyl-benzyl)-[2-(4-chloro-3-trifluoromethyl-phenyl)-ethyl]-amide | 5-methyl-1H-pyrrolo[2,3-c]pyridine-7-carboxylic acid ethyl ester | (4-tert-butyl-benzyl)-[2-(4-chloro-3-trifluoromethyl-phenyl)-ethyl]-amine | MS (ISP) 528.4 (M + H)$^+$ |
| B1.15 | 5-methyl-1H-pyrrolo[2,3-c]pyridine-7-carboxylic acid (4-tert-butyl-benzyl)-[2-(3-chloro-4-fluoro-phenyl)-ethyl]-amide | 5-methyl-1H-pyrrolo[2,3-c]pyridine-7-carboxylic acid ethyl ester | (4-tert-butyl-benzyl)-[2-(3-chloro-4-fluoro-phenyl)-ethyl]-amine | MS (ISP) 478.4 (M + H)$^+$ |

-continued

| No. | compound of formula I | starting material of formula II | starting material of formula III | MS (ISP) |
|---|---|---|---|---|
| B1.16 | 5-Methyl-1H-pyrrolo[2,3-c]pyridine-7-carboxylic acid (4-tert-butyl-benzyl)-[2-(3-fluoro-5-trifluoromethyl-phenyl)-ethyl]-amide | 5-methyl-1H-pyrrolo[2,3-c]pyridine-7-carboxylic acid ethyl ester | (4-tert-butyl-benzyl)-[2-(3-fluoro-5-trifluoromethyl-phenyl)-ethyl]-amine | MS (ISP) 512.5 $(M + H)^+$ |
| B1.17 | 5-Methyl-1H-pyrrolo[2,3-c]pyridine-7-carboxylic acid (4-tert-butyl-benzyl)-phenethyl-amide | 5-methyl-1H-pyrrolo[2,3-c]pyridine-7-carboxylic acid ethyl ester | (4-tert-butyl-benzyl)-phenethyl-amine | MS (ISP) 426.4 $(M + H)^+$ |
| B1.18 | 5-methyl-1H-pyrrolo[2,3-c]pyridine-7-carboxylic acid (4-tert-butyl-benzyl)-[2-(3-difluoromethoxy-phenyl)-ethyl]-amide | 5-methyl-1H-pyrrolo[2,3-c]pyridine-7-carboxylic acid ethyl ester | (4-tert-butyl-benzyl)-[2-(3-difluoromethoxy-phenyl)-ethyl]-amine | MS (ISP) 492.5 $(M + H)^+$ |
| B1.19 | 5-methyl-1H-pyrrolo[2,3-c]pyridine-7-carboxylic acid (4-tert-butyl-benzyl)-[2-(4-fluoro-3-trifluoromethyl-phenyl)-ethyl]-amide | 5-methyl-1H-pyrrolo[2,3-c]pyridine-7-carboxylic acid ethyl ester | (4-tert-butyl-benzyl)-[2-(4-fluoro-3-trifluoromethyl-phenyl)-ethyl]-amine | MS (ISP) 512.5 $(M + H)^+$ |
| B1.20 | 5-methyl-1H-pyrrolo[2,3-c]pyridine-7-carboxylic acid (4-tert-butyl-benzyl)-[2-(3-trifluoromethyl-phenyl)-ethyl]-amide | 5-methyl-1H-pyrrolo[2,3-c]pyridine-7-carboxylic acid ethyl ester | (4-tert-butyl-benzyl)-[2-(3-trifluoromethyl-phenyl)-ethyl]-amine | MS (ISP) 494.5 $(M + H)^+$ |

EXAMPLE B2

1H-Pyrrolo[2,3-c]pyridine-7-carboxylic acid (4-tert-butyl-benzyl)-[2-(3-difluoromethoxy-phenyl)-ethyl]-amide (B2.1)

(4-tert-Butyl-benzyl)-[2-(3-difluoromethoxy-phenyl)-ethyl]-amine (90 mg, 0.27 mmol), N-methylmorpholine (74 mg, 0.73 mmol), and HBTU (139 mg, 0.37 mmol) were added at RT to a solution of 1H-pyrrolo[2,3-c]pyridine-7-carboxylic acid (66 mg) in DMF (3 mL), then after 64 h the reaction mixture was partitioned between water and ethyl acetate. The organic layer was washed with brine, dried (MgSO$_4$), and evaporated. Chromatography of the residue (SiO$_2$, heptane-dichloromethane gradient) afforded the title compound (108 mg, 86% over 2 steps). Light yellow oil, MS (ISP) 478.4 $(M+H)^+$.

EXAMPLE B3

4-Fluoro-1H-pyrrolo[2,3-c]pyridine-7-carboxylic acid (4-tert-butyl-benzyl)-[2-(4-chloro-3-trifluoromethyl-phenyl)-ethyl]-amide (B3.1)

A solution of 4-fluoro-1H-pyrrolo[2,3-c]pyridine-7-carboxylic acid ethyl ester (50 mg, 0.24 mmol) in THF (0.7 mL) was treated with 2 M aq. potassium hydroxide solution (0.24 mL, 0.48 mmol) and stirred for 90 min at RT. The reaction mixture was then evaporated, the residue dissolved in DMF (3.2 mL) and treated with (4-tert-butyl-benzyl)-[2-(4-chloro-3-trifluoromethyl-phenyl)-ethyl]-amine (98 mg, 0.26 mmol), N-methylmorpholine (73 mg, 0.72 mmol), and HBTU (137 mg, 0.36 mmol). After 16 h, the reaction mixture was partitioned between water and ethyl acetate, the organic layer was washed with brine, dried (MgSO$_4$), and evaporated. Chromatography of the residue (SiO$_2$, heptane/ethyl acetate 97:3) afforded the title compound (95 mg, 74%). White foam, MS (ISP) 532.3 $(M+H)^+$.

In analogy with the above procedure the following compounds were prepared:

| | compound of formula I | starting material of formula II | starting material of formula III | MS (ISP) $(M + H)^+$ |
|---|---|---|---|---|
| B3.2 | 5-trifluoromethyl-1H-pyrrolo[2,3-c]pyridine-7-carboxylic acid (4-tert-butyl-benzyl)-[2-(4-chloro-3-trifluoromethyl-phenyl)-ethyl]-amide | 5-trifluoromethyl-1H-pyrrolo[2,3-c]pyridine-7-carboxylic acid ethyl ester | (4-tert-butyl-benzyl)-[2-(4-chloro-3-trifluoromethyl-phenyl)-ethyl]-amine | 582.3 |
| B3.3 | 4-fluoro-1H-pyrrolo[2,3-c]pyridine-7-carboxylic acid (4-tert-butyl-benzyl)-[2-(4-fluoro-3-trifluoromethyl-phenyl)-ethyl]-amide | 4-fluoro-1H-pyrrolo[2,3-c]pyridine-7-carboxylic acid ethyl ester | (4-tert-butyl-benzyl)-[2-(4-fluoro-3-trifluoromethyl-phenyl)-ethyl]-amine | 516.3 |

| | compound of formula I | starting material of formula II | starting material of formula III | MS (ISP) (M + H)+ |
|---|---|---|---|---|
| B3.4 | 4-fluoro-1H-pyrrolo[2,3-c]pyridine-7-carboxylic acid (4-tert-butyl-benzyl)-[2-(3-trifluoromethyl-phenyl)-ethyl]-amide | 4-fluoro-1H-pyrrolo[2,3-c]pyridine-7-carboxylic acid ethyl ester | (4-tert-butyl-benzyl)-[2-(3-trifluoromethyl-phenyl)-ethyl]-amine | 498.5 |
| B3.5 | 4-fluoro-1H-pyrrolo[2,3-c]pyridine-7-carboxylic acid (4-tert-butyl-benzyl)-[2-(3,4-dichloro-phenyl)-ethyl]-amide | 4-fluoro-1H-pyrrolo[2,3-c]pyridine-7-carboxylic acid ethyl ester | (4-tert-butyl-benzyl)-[2-(3,4-dichlorophenyl)-ethyl]-amine | 498.1 |
| B3.6 | 4-fluoro-1H-pyrrolo[2,3-c]pyridine-7-carboxylic acid (4-tert-butyl-benzyl)-[2-(3-trifluoromethoxyphenyl)-ethyl]-amide | 4-fluoro-1H-pyrrolo[2,3-c]pyridine-7-carboxylic acid ethyl ester | (4-tert-butyl-benzyl)-[2-(3-trifluoromethoxyphenyl)-ethyl]-amine | 514.3 |
| B3.7 | 4-fluoro-1H-pyrrolo[2,3-c]pyridine-7-carboxylic acid (4-tert-butyl-benzyl)-(2-p-tolyl-ethyl)-amide | 4-fluoro-1H-pyrrolo[2,3-c]pyridine-7-carboxylic acid ethyl ester | (4-tert-butyl-benzyl)-(2-p-tolyl-ethyl)-amine | 444.5 |
| B3.8 | 5-trifluoromethyl-1H-pyrrolo[2,3-c]pyridine-7-carboxylic acid (4-tert-butyl-benzyl)-[2-(4-fluoro-3-trifluoromethyl-phenyl)-ethyl]-amide | 5-trifluoromethyl-1H-pyrrolo[2,3-c]pyridine-7-carboxylic acid ethyl ester | (4-tert-butyl-benzyl)-[2-(4-fluoro-3-trifluoromethyl-phenyl)-ethyl]-amine | 566.3 |
| B3.9 | 5-trifluoromethyl-1H-pyrrolo[2,3-c]pyridine-7-carboxylic acid (4-tert-butyl-benzyl)-[2-(3-trifluoromethyl-phenyl)-ethyl]-amide | 5-trifluoromethyl-1H-pyrrolo[2,3-c]pyridine-7-carboxylic acid ethyl ester | (4-tert-butyl-benzyl)-[2-(3-trifluoromethyl-phenyl)-ethyl]-amine | 548.5 |
| B3.10 | 5-trifluoromethyl-1H-pyrrolo[2,3-c]pyridine-7-carboxylic acid (4-tert-butyl-benzyl)-[2-(3,4-dichloro-phenyl)-ethyl]-amide | 5-trifluoromethyl-1H-pyrrolo[2,3-c]pyridine-7-carboxylic acid ethyl ester | (4-tert-butyl-benzyl)-[2-(3,4-dichlorophenyl)-ethyl]-amine | 548.3 |
| B3.11 | 5-trifluoromethyl-1H-pyrrolo[2,3-c]pyridine-7-carboxylic acid (4-tert-butyl-benzyl)-[2-(3-trifluoromethoxyphenyl)-ethyl]-amide | 5-trifluoromethyl-1H-pyrrolo[2,3-c]pyridine-7-carboxylic acid ethyl ester | (4-tert-butyl-benzyl)-[2-(3-trifluoromethoxyphenyl)-ethyl]-amine | 564.5 |
| B3.12 | 5-trifluoromethyl-1H-pyrrolo[2,3-c]pyridine-7-carboxylic acid (4-tert-butyl-benzyl)-(2-p-tolyl-ethyl)-amide | 5-trifluoromethyl-1H-pyrrolo[2,3-c]pyridine-7-carboxylic acid ethyl ester | (4-tert-butyl-benzyl)-(2-p-tolyl-ethyl)-amine | 494.4 |
| B3.13 | 4-methyl-1H-pyrrolo[2,3-c]pyridine-7-carboxylic acid (4-tert-butyl-benzyl)-[2-(3,4-dichloro-phenyl)-ethyl]-amide | 4-methyl-1H-pyrrolo[2,3-c]pyridine-7-carboxylic acid ethyl ester | (4-tert-butyl-benzyl)-[2-(3,4-dichloro-phenyl)-ethyl]-amine | 494.5 |
| B3.14 | 5-methyl-1H-pyrrolo[2,3-c]pyridine-7-carboxylic acid (4-tert-butyl-benzyl)-[2-(3,4-dichloro-phenyl)-ethyl]-amide | 5-methyl-1H-pyrrolo[2,3-c]pyridine-7-carboxylic acid ethyl ester | (4-tert-butyl-benzyl)-[2-(3,4-dichloro-phenyl)-ethyl]-amine | 494.5 |
| B3.15 | 4-fluoro-1H-pyrrolo[2,3-c]pyridine-7-carboxylic acid (4-tert-butyl-benzyl)-[2-(4-fluoro-phenyl)-ethyl]-amide | 5-methyl-1H-pyrrolo[2,3-c]pyridine-7-carboxylic acid ethyl ester | (4-tert-butyl-benzyl)-[2-(4-fluoro-3-trifluoromethyl-phenyl)-ethyl]-amine | 448.4 |
| B3.16 | 1H-pyrazolo[3,4-c]pyridine-7-carboxylic acid (4-tert-butyl-benzyl)-[2-(3,4-dichloro-phenyl)-ethyl]-amide | 1H-pyrazolo[3,4-c]pyridine-7-carboxylic acid ethyl ester | (4-tert-butyl-benzyl)-[2-(3,4-dichloro-phenyl)-ethyl]-amine | 481.0 |
| B3.17 | 1H-pyrazolo[3,4-c]pyridine-7-carboxylic acid (4-tert-butyl-benzyl)-[2-(4-chloro-3-trifluoromethyl-phenyl)-ethyl]-amide | 1H-pyrazolo[3,4-c]pyridine-7-carboxylic acid ethyl ester | (4-tert-butyl-benzyl)-[2-(4-chloro-3-trifluoromethyl-phenyl)-ethyl]-amine | 515.0 |

-continued

| | compound of formula I | starting material of formula II | starting material of formula III | MS (ISP) (M + H)+ |
|---|---|---|---|---|
| B3.18 | 1H-pyrazolo[3,4-c]pyridine-7-carboxylic acid (4-tert-butyl-benzyl)-[2-(3-trifluoromethyl-phenyl)-ethyl]-amide | 1H-pyrazolo[3,4-c]pyridine-7-carboxylic acid ethyl ester | (4-tert-butyl-benzyl)-[2-(3-trifluoromethyl-phenyl)-ethyl]-amine | 481.1 |
| B3.19 | 5-chloro-1H-pyrrolo[2,3-c]pyridine-7-carboxylic acid (4-tert-butyl-benzyl)-[2-(3,4-dichloro-phenyl)-ethyl]-amide | 5-chloro-1H-pyrrolo[2,3-c]pyridine-7-carboxylic acid ethyl ester | (4-tert-butyl-benzyl)-[2-(3,4-dichloro-phenyl)-ethyl]-amine | 514.2 |
| B3.20 | 5-chloro-1H-pyrrolo[2,3-c]pyridine-7-carboxylic acid (4-tert-butyl-benzyl)-[2-(4-fluoro-phenyl)-ethyl]-amide | 5-chloro-1H-pyrrolo[2,3-c]pyridine-7-carboxylic acid ethyl ester | (4-tert-butyl-benzyl)-[2-(4-fluoro-3-trifluoromethyl-phenyl)-ethyl]-amine | 464.2 |
| B3.21 | 5-chloro-1H-pyrrolo[2,3-c]pyridine-7-carboxylic acid (4-tert-butyl-benzyl)-[2-(3-trifluoromethoxyphenyl)-ethyl]-amide | 5-chloro-1H-pyrrolo[2,3-c]pyridine-7-carboxylic acid ethyl ester | (4-tert-butyl-benzyl)-[2-(3-trifluoromethoxyphenyl)-ethyl]-amine | 530.2 |
| B3.22 | 5-chloro-1H-pyrrolo[2,3-c]pyridine-7-carboxylic acid (4-tert-butyl-benzyl)-[2-(3-trifluoromethyl-phenyl)-ethyl]-amide | 5-chloro-1H-pyrrolo[2,3-c]pyridine-7-carboxylic acid ethyl ester | (4-tert-butyl-benzyl)-[2-(3-trifluoromethoxyphenyl)-ethyl]-amine | 514.3 |
| B3.23 | 5-methyl-1H-pyrrolo[2,3-c]pyridine-7-carboxylic acid (4-tert-butyl-benzyl)-{2-[(4-chloro-phenyl)-methyl-amino]-ethyl}-amide | 5-methyl-1H-pyrrolo[2,3-c]pyridine-7-carboxylic acid ethyl ester | N'-(4-tert-butyl-benzyl)-N-(4-chloro-phenyl)-N-methyl-ethane-1,2-diamine | 489.2 |
| B3.24 | 5-methyl-1H-pyrrolo[2,3-c]pyridine-7-carboxylic acid butyl-(4-tert-butyl-benzyl)-amide | 5-methyl-1H-pyrrolo[2,3-c]pyridine-7-carboxylic acid ethyl ester | butyl-(4-tert-butyl-benzyl)-amine | 378.4 |

EXAMPLE B4

7-{(4-tert-Butyl-benzyl)-[2-(3,4-dichloro-phenyl)-ethyl]-carbamoyl}-1H-pyrrolo[2,3-c]pyridine-5-carboxylic acid methyl ester (B4.1)

A solution of 5-chloro-1H-pyrrolo[2,3-c]pyridine-7-carboxylic acid (4-tert-butyl-benzyl)-[2-(3,4-dichloro-phenyl)-ethyl]-amide (112 mg, 0.218 mmol), triethylamine (55 mg, 0.54 mmol), and 1,1'-bis(diphenylphosphino)ferrocene-palladium(II)dichloride dichloromethane complex (28 mg, 34 µmol) in methanol (1.5 mL) and toluene (1.5 mL) was stirred for 24 h at 130° C. under a carbon monoxide atmosphere (50 bar). After cooling and evaporation of volatile material, the residue was chromatographed ($SiO_2$, heptane-dichloromethane gradient), to afford the title compound (1 mg, 9%). Light yellow oil, MS (ISP) 538.3 (M+H)+.

The compounds of formula I are cholesteryl ester transfer protein (CETP) inhibitors. Atherosclerosis and its associated coronary heart disease is the leading cause of death in the industrialized world. Risk for development of coronary heart disease has been shown to be strongly correlated with certain plasma lipid levels. Lipids are transported in the blood by lipoproteins. The general structure of lipoproteins is a core of neutral lipids (triglyceride and cholesterol ester) and an envelope of polar lipids (phospholipids and non esterified cholesterol). There are three different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

Plasma lipoprotein metabolism can be described as a flux of cholesterol between liver and the other tissues. The LDL pathway corresponds to the secretion of VLDL from the liver to deliver cholesterol by LDL to tissues. Any alteration in LDL catabolism could lead to uptake of excess cholesterol in the vessel wall forming foam cells and atherosclerosis. The opposite pathway is the mobilization of free cholesterol from peripheral tissues by HDL to deliver cholesterol to the liver to be eventually excreted with bile. In humans a significant part of cholesteryl ester (CE) is transferred from HDL to the VLDL, LDL pathway. This transfer is mediated by a 70,000 dalton plasma glycoprotein, the cholesteryl ester transfer protein (CETP).

Mutations in the CETP gene associated with CETP deficiency are characterized by high HDL-cholesterol levels (>60 mg/dL) and reduced cardiovascular risk. Such findings are consistent with studies of pharmacologically mediated inhibition of CETP in the rabbit, which argue strongly in favor of CETP inhibition as a valid therapeutic approach [Le Goff et al., Pharmacology & Therapeutics 101:17-38 (2004); Okamoto et al., Nature 406:203-207 2000)].

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (-10-12%). As a result, there is a significant unmet medical need for a well tolerated agent which can significantly elevate plasma HDL levels. The net result of CETP activity is a lowering of HDL-C and an increase in LDL-C. This effect on lipoprotein profile is believed to be pro-atherogenic, especially in subjects whose lipid profile constitutes an increased risk for coronary heart disease. Therefore by inhibiting CETP activity there is the potential to inverse this relationship towards a lower risk and ultimately to protect against coronary heart diseases and associated mortality.

Thus, CETP inhibitors are useful as medicaments for the treatment and/or prophylaxis of atherosclerosis, peripheral vascular disease, dyslipidemia, hyperbeta-lipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In addition, CETP inhibitors may be used in combination with another compound, said compound being an HMG-CoA reductase inhibitor, a microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant.

As described above, the compounds of formula I of the present invention can be used as medicaments for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxermia. The use as medicament for the treatment and/or prevention of dyslipidemia is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In another embodiment, the invention relates to a method for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. A method for the treatment and/or prophylaxis of dyslipidemia is preferred.

The invention further relates to the use of compounds of formula I as defined above for the treatment and/or prophylaxis of diseases are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the treatment and/or prophylaxis of dyslipidemia is preferred.

In addition, the invention relates to the use of compounds of formula I as defined above for the preparation of medicaments for the treatment and/or prophylaxis of diseases are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the preparation of medicaments for the treatment and/or prophylaxis of dyslipidemia is preferred.

In addition, CETP inhibitors are useful in combination with another compound, said compound being an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant.

The invention therefore also relates to pharmaceutical compositions comprising a compound of formula I as defined above in combination with an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant, as well as a pharmaceutically acceptable carrier and/or adjuvant.

The invention further relates to the use of compounds of formula I as defined above in combination with an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant for the treatment and/or prophylaxis of diseases such as atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia, as well as to the use of such a combination for the preparation of corresponding medicaments.

The compounds of formula I and their pharmaceutically acceptable salts possess valuable pharmacological properties. Specifically, it has been found that the compounds of the present invention are inhibitors of the cholesteryl ester transfer protein (CETP).

The following tests were carried out in order to determine the activity of the compounds of formula I.

Activity of CETP inhibitors was determined using a buffer assay system. Partially purified CETP transferred radiolabeled cholesteryl ester from HDL donor particles to biotin-labeled LDL acceptor particles. The reaction was stopped by addition of streptavidin-coupled scintillation proximity assay (SPA) beads. These beads captured the biotinylated acceptor particles and transferred radioactivity was measured. The assay system was purchased and performed according to manufacturer's recommendations (Amersham Biosciences). Inhibitory activity of compounds was determined as percentage of positive control activity containing CETP together with donor and acceptor particles. Serial dilution of compounds was performed in order to determine the $IC_{50}$ values.

Activity of the compounds was subsequently measured in the presence of plasma using the same assay as described above except that the source of CETP was human lipoprotein-deprived serum (LPDS). Inhibitory activity of compounds was determined as percentage of positive control activity containing all the assay components except compound. Serial dilution of compounds was performed in order to determine the $IC_{50}$ values.

Under the latter assay conditions, the compounds of the present invention exhibit $IC_{50}$ values within the range of about 1 nM to about 10 μM, e.g., of about 1 nM to about 1 μM, e.g., of about 1 nM to about 200 nM. The following table shows measured values for some selected compounds of the present invention.

|  | $IC_{50}$ (nM) |
|---|---|
| Compound 3.14 | 141 |
| Compound 3.15 | 437 |
| Compound 3.22 | 175 |

In vivo activity of the compounds of formula I was determined in hamster using the following protocol:

Male golden Syrian hamsters (6-week-old, 100-130 g) under standard chow diet received compounds in the morning by oral gavage using appropriate vehicle, blood was taken 2 h later by retro-orbital bleeding under isofluran anaesthesia and 7 h later on sacrificed animals. Plasma was separated from blood using low speed centrifugation and CETP activity was measured in plasma using the radioactive CETP activity assay as described above except that diluted plasma replaced LPDS. In vivo CETP inhibition was expressed as CETP activity remaining in the plasma of treated animals as compared to plasma CETP activity of placebo treated animals.

Efficacy of compounds in modulating plasma lipid levels is determined in hamsters after 7 days of daily administration of compounds. Male hamsters are acclimated for 3-4 days to receive food as a paste made of 10 g chow and 10 g water per day. Compounds are then mixed within this paste and a portion containing the proper amount of compounds is given every morning for 7 days. Alternatively compounds can be given by oral gavage using the proper vehicle. Blood is taken before compound treatment by retro-orbital bleeding and at the end of the treatment on sacrificed animals. Plasma is separated from blood by low speed centrifugation and selected organs are taken (e.g liver, fat, brain, etc.). Effects of compounds on plasma lipid levels are determined by measuring total cholesterol, HDL-cholesterol, LDL-cholesterol and triglyceride using colorimetric enzymatic assays (Roche Diagnostic GmbH, Mannheim, Germany). HDL-C, LDL-C and VLDL-C are e.g., quantified using size exclusion chromatography on superpose-6 column using SMART™ system (Pharmacia). Lipoprotein distribution is calculated assuming a Gaussian distribution for each peak, using a non-linear, least-squares curve-fitting procedure to calculate the area under the curve. Plasma samples are also used to quantify CETP activity as described above. Compound concentration is also determined in plasma and selected tissues as liver, fat, heart, muscle and brain.

Efficacy of compounds in modulating plasma lipid levels is also determined in cholesterol/fat fed hamsters. The protocol is identical as described above except that animals are fed with chow diet enriched with 10% (w/w) saturated fat and 0.05% (w/w) cholesterol. Animals receive this high fat diet 2 weeks before starting compound administration and continue this diet throughout the study. The 2 weeks pre-treatment induces an increase in plasma cholesterol and triglyceride levels allowing a better assessment of LDL-C and triglyceride lowering.

Efficacy of compounds in its ability to acutely raise HDL-C can be assessed in cynomolgus monkeys. Animals are fed with standard primate maintenance diet. Compounds are formulated with appropriate vehicle and administered to animals by oral gavage. Blood is taken before and at several time-points after compound administration (usually 30 min, 1 h, 2 h, 4 h, 7 h and 24 h). Plasma is separated from blood by low speed centrifugation and CETP activity and plasma lipids are quantified. Compound potency and efficacy can be assessed by measuring the HDL-C increase after this single-dose administration. In such pharmacodynamic model the extent together with the kinetics of the pharmacologic effect can be assessed.

The compounds of formula I and their pharmaceutically acceptable salts and esters can be used as medicaments, e.g. in the form of pharmaceutical preparations for enteral, parenteral or topical administration. They can be administered, e.g., perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, e.g., lactose, corn starch or derivatives thereof, talc, stearic acid or its salts can be used as carrier materials for tablets, coated tablets, dragées and hard gelatine capsules. Suitable carrier materials for soft gelatine capsules are, e.g., vegetable oils, waxes, fats and semi-solid and liquid polyols (depending on the nature of the active ingredient no carriers are, however, required in the case of soft gelatine capsules). Suitable carrier materials for the production of solutions and syrups are, e.g., water, polyols, sucrose, invert sugar and the like. Suitable carrier materials for injection solutions are, e.g., water, alcohols, polyols, glycerol and vegetable oils. Suitable carrier materials for suppositories are, e.g., natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, e.g., 0.5-100 mg, of a compound of formula I.

The following examples serve to illustrate the present invention in more detail. They are, however, not intended to limit its scope in any manner.

EXAMPLE A

Film Coated Tablets

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

EXAMPLE B

Capsules

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

EXAMPLE C

Injection Solutions

| | |
| --- | --- |
| Compound of formula (I) | 3.0 mg |
| Gelatin | 150.0 mg |
| Phenol | 4.7 mg |
| Sodium carbonate | to obtain a final pH of 7 |
| Water for injection solutions | ad 1.0 ml |

EXAMPLE D

Soft Gelatin Capsules

| | |
| --- | --- |
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

The invention claimed is:

1. A compound of formula (I):

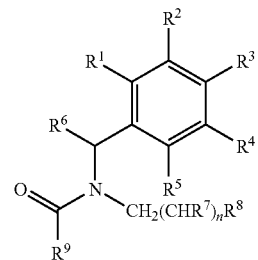

or a pharmaceutically acceptable salt thereof, wherein:
$R^1$, $R^2$, $R^4$ and $R^5$ are independently from each other hydrogen, $C_1$-$C_6$alkyl, $C_1$-$C_6$alkoxy or halogen;
$R^3$ is $C_1$-$C_6$alkyl, $C_1$-$C_6$alkoxy, aryloxy, $C_3$-$C_7$cycloalkyl or pentafluorosulphuranyl;
$R^6$ is hydrogen or $C_1$-$C_6$alkyl;
$R^7$ is hydrogen, $C_1$-$C_6$alkyl, hydroxy or halogen;
$R^8$ is selected from the group consisting of: (1) $C_1$-$C_6$alkyl, (2) $C_2$-$C_6$alkenyl, (3) halogen-$C_1$-$C_6$alkyl, (4) phenyl optionally substituted by one to three substituents independently selected from the group consisting of hydrogen, halogen, $C_1$-$C_6$alkyl, halogen-$C_1$-$C_6$alkyl and halogen-$C_1$-$C_6$alkoxy, (5) —$OR^{10}$, wherein $R^{10}$ is C$_1$-C$_6$alkyl or phenyl wherein said phenyl is optionally substituted by one to three substituents independently selected from the group consisting of hydrogen, halogen, C$_1$-C$_6$alkyl, halogen-C$_1$-C$_6$alkyl and halogen-C$_1$-C$_6$alkoxy, (6) —NR$^{11}$R$^{12}$, wherein R$^{11}$ and R$^{12}$ independently from each other are selected from the group consisting of hydrogen, C$_1$-C$_6$alkyl, and phenyl wherein said phenyl is optionally substituted by one to three substituents independently selected from the group consisting of hydrogen, halogen, C$_1$-C$_6$alkyl, halogen-C$_1$-C$_6$alkyl and halogen-C$_1$-C$_6$alkoxy, and (7) —C(O)—OR$^{13}$, wherein R$^{13}$ is hydrogen or C$_1$-C$_6$alkyl;

R$^9$ is 1H-pyrrolo[2,3-c]pyridin-7-yl which is unsubstituted or substituted by one or two substituents independently selected from the group consisting of halogen, C$_1$-C$_6$alkyl, halogen-C$_1$-C$_6$alkyl and C(O)OCH$_3$; and n is 1, 2 or 3.

2. A compound of formula (I) according to claim 1 as illustrated in formula (Ia):

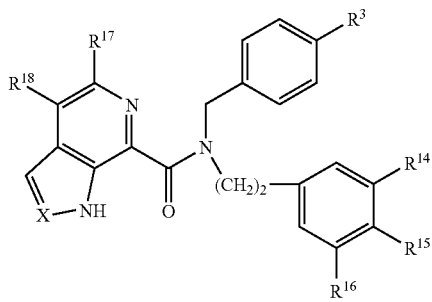

(Ia)

wherein:
R$^3$ is C$_1$-C$_6$alkyl;
R$^{14}$, R$^{15}$ and R$^{16}$ are independently hydrogen, halogen, C$_1$-C$_6$alkyl, halogen-C$_1$-C$_6$alkyl or halogen-C$_1$-C$_6$alkoxy;
R$^{17}$ and R$^{18}$ are independently hydrogen, halogen, C$_1$-C$_6$alkyl, halogen-C$_1$-C$_6$alkyl or C(O)OCH$_3$; and
X is CH.

3. A compound of formula (I) according to claim 1 as illustrated in formula (Ib):

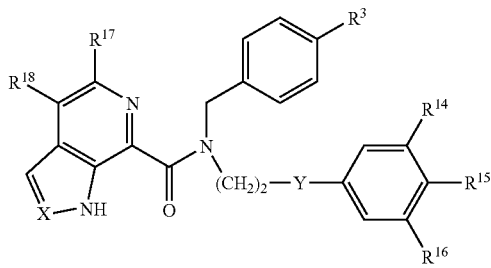

(Ib)

wherein:
R$^3$ is C$_1$-C$_6$alkyl;
R$^{14}$, R$^{15}$ and R$^{16}$ are independently hydrogen, halogen, C$_1$-C$_6$alkyl, halogen-C$_1$-C$_6$alkyl or halogen-C$_1$-C$_6$alkoxy;
R$^{17}$ and R$^{18}$ are independently hydrogen, halogen, C$_1$-C$_6$alkyl, halogen-C$_1$-C$_6$alkyl or C(O)OCH$_3$;
X is CH; and
Y is O, N—H, or N(C$_1$-C$_6$alkyl).

4. A compound of formula (I) according to claim 1 as illustrated in formula (Ic):

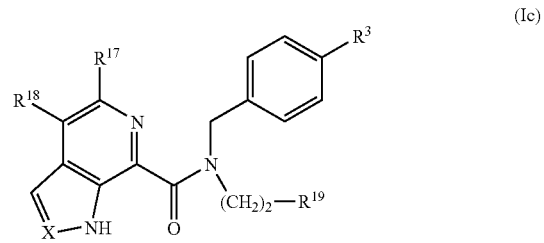

(Ic)

wherein:
R$^3$ is C$_1$-C$_6$alkyl;
R$^{17}$ and R$^{18}$ are independently hydrogen, halogen, C$_1$-C$_6$alkyl, halogen-C$_1$-C$_6$alkyl or C(O)OCH$_3$;
R$^{19}$ is C$_1$-C$_6$alkyl, O—C$_1$-C$_6$alkyl, N(H)—C$_1$-C$_6$alkyl or N(C$_1$-C$_6$alkyl)-C$_1$-C$_6$alkyl; and
X is CH.

5. A compound of claim 1 selected from the group consisting of:
1H-pyrrolo[2,3-c]pyridine-7-carboxylic acid (4-tert-butyl-benzyl)-[2-(4-fluoro-3-trifluoromethyl-phenyl)-ethyl]-amide,
1H-pyrrolo[2,3-c]pyridine-7-carboxylic acid (4-tert-butyl-benzyl)-[2-(3-trifluoromethyl-phenyl)-ethyl]-amide,
1H-pyrrolo[2,3-c]pyridine-7-carboxylic acid (4-tert-butyl-benzyl)-[2-(3,4-dichloro-phenyl)-ethyl]-amide,
1H-pyrrolo[2,3-c]pyridine-7-carboxylic acid (4-tert-butyl-benzyl)-[2-(4-fluoro-phenyl)-ethyl]-amide,
1H-pyrrolo[2,3-c]pyridine-7-carboxylic acid (4-tert-butyl-benzyl)-(2-p-tolyl-ethyl)-amide,
1H-pyrrolo[2,3-c]pyridine-7-carboxylic acid (4-tert-butyl-benzyl)-[2-(3-trifluoromethoxy-phenyl)-ethyl]-amide,
1H-pyrrolo[2,3-c]pyridine-7-carboxylic acid (4-tert-butyl-benzyl)-[2-(3-chloro-4-fluoro-phenyl)-ethyl]-amide,
1H-pyrrolo[2,3-c]pyridine-7-carboxylic acid (4-tert-butyl-benzyl)-[2-(4-chloro-3-trifluoromethyl-phenyl)-ethyl]-amide,
1H-pyrrolo[2,3-c]pyridine-7-carboxylic acid (4-tert-butyl-benzyl)-[2-(3-fluoro-5-trifluoromethyl-phenyl)-ethyl]-amide,
1H-pyrrolo[2,3-c]pyridine-7-carboxylic acid (4-tert-butyl-benzyl)-phenethyl-amide,
5-methyl-1H-pyrrolo[2,3-c]pyridine-7-carboxylic acid (4-tert-butyl-benzyl)-[2-(4-fluoro-phenyl)-ethyl]-amide,
5-methyl-1H-pyrrolo[2,3-c]pyridine-7-carboxylic acid (4-tert-butyl-benzyl)-(2-p-tolyl-ethyl)-amide,
5-methyl-1H-pyrrolo[2,3-c]pyridine-7-carboxylic acid (4-tert-butyl-benzyl)-[2-(3-trifluoromethoxy-phenyl)-ethyl]-amide,
5-methyl-1H-pyrrolo[2,3-c]pyridine-7-carboxylic acid (4-tert-butyl-benzyl)-[2-(4-chloro-3-trifluoromethyl-phenyl)-ethyl]-amide,
1H-pyrrolo[2,3-c]pyridine-7-carboxylic acid (4-tert-butyl-benzyl)-[2-(3-difluoromethoxy-phenyl)-ethyl]-amide, 5-methyl-1H-pyrrolo[2,3-c]pyridine-7-carboxylic acid (4-tert-butyl-benzyl)-[2-(3-chloro-4-fluoro-phenyl)-ethyl]-amide,
5-methyl-1H-pyrrolo[2,3-c]pyridine-7-carboxylic acid (4-tert-butyl-benzyl)-[2-(3-fluoro-5-trifluoromethyl-phenyl)-ethyl]-amide,
5-methyl-1H-pyrrolo[2,3-c]pyridine-7-carboxylic acid (4-tert-butyl-benzyl)-phenethyl-amide,
5-methyl-1H-pyrrolo[2,3-c]pyridine-7-carboxylic acid (4-tert-butyl-benzyl)-[2-(3-difluoromethoxy-phenyl)-ethyl]-amide,
5-methyl-1H-pyrrolo[2,3-c]pyridine-7-carboxylic acid (4-tert-butyl-benzyl)-[2-(4-fluoro-3-trifluoromethyl-phenyl)-ethyl]-amide,
5-methyl-1H-pyrrolo[2,3-c]pyridine-7-carboxylic acid (4-tert-butyl-benzyl)-[2-(3-trifluoromethyl-phenyl)-ethyl]-amide,
4-fluoro-1H-pyrrolo[2,3-c]pyridine-7-carboxylic acid (4-tert-butyl-benzyl)-[2-(4-chloro-3-trifluoromethyl-phenyl)-ethyl]-amide,
5-trifluoromethyl-1H-pyrrolo[2,3-c]pyridine-7-carboxylic acid (4-tert-butyl-benzyl)-[2-(4-chloro-3-trifluoromethyl-phenyl)-ethyl]-amide,
4-fluoro-1H-pyrrolo[2,3-c]pyridine-7-carboxylic acid (4-tert-butyl-benzyl)-[2-(4-fluoro-3-trifluoromethyl-phenyl)-ethyl]-amide,
4-fluoro-1H-pyrrolo[2,3-c]pyridine-7-carboxylic acid (4-tert-butyl-benzyl)-[2-(3-trifluoromethyl-phenyl)-ethyl]-amide,
4-fluoro-1H-pyrrolo[2,3-c]pyridine-7-carboxylic acid (4-tert-butyl-benzyl)-[2-(3,4-dichloro-phenyl)-ethyl]-amide,
4-fluoro-1H-pyrrolo[2,3-c]pyridine-7-carboxylic acid (4-tert-butyl-benzyl)-[2-(3-trifluoromethoxy-phenyl)-ethyl]-amide,
4-fluoro-1H-pyrrolo[2,3-c]pyridine-7-carboxylic acid (4-tert-butyl-benzyl)-(2-p-tolyl-ethyl)-amide,
5-trifluoromethyl-1H-pyrrolo[2,3-c]pyridine-7-carboxylic acid (4-tert-butyl-benzyl)-[2-(4-fluoro-3-trifluoromethyl-phenyl)-ethyl]-amide,
5-trifluoromethyl-1H-pyrrolo[2,3-c]pyridine-7-carboxylic acid (4-tert-butyl-benzyl)-[2-(3-trifluoromethyl-phenyl)-ethyl]-amide,
5-trifluoromethyl-1H-pyrrolo[2,3-c]pyridine-7-carboxylic acid (4-tert-butyl-benzyl)-[2-(3,4-dichloro-phenyl)-ethyl]-amide,
5-trifluoromethyl-1H-pyrrolo[2,3-c]pyridine-7-carboxylic acid (4-tert-butyl-benzyl)-[2-(3-trifluoromethoxy-phenyl)-ethyl]-amide,
5-trifluoromethyl-1H-pyrrolo[2,3-c]pyridine-7-carboxylic acid (4-tert-butyl-benzyl)-(2-p-tolyl-ethyl)-amide,
4-methyl-1H-pyrrolo[2,3-c]pyridine-7-carboxylic acid (4-tert-butyl-benzyl)-[2-(3,4-dichloro-phenyl)-ethyl]-amide,
5-methyl-1H-pyrrolo[2,3-c]pyridine-7-carboxylic acid (4-tert-butyl-benzyl)-[2-(3,4-dichloro-phenyl)-ethyl]-amide,
4-fluoro-1H-pyrrolo[2,3-c]pyridine-7-carboxylic acid (4-tert-butyl-benzyl)-[2-(4-fluoro-phenyl)-ethyl]-amide,
5-chloro-1H-pyrrolo[2,3-c]pyridine-7-carboxylic acid (4-tert-butyl-benzyl)-[2-(3,4-dichloro-phenyl)-ethyl]-amide,
5-chloro-1H-pyrrolo[2,3-c]pyridine-7-carboxylic acid (4-tert-butyl-benzyl)-[2-(4-fluoro-phenyl)-ethyl]-amide,
5-chloro-1H-pyrrolo[2,3-c]pyridine-7-carboxylic acid (4-tert-butyl-benzyl)-[2-(3-trifluoromethoxy-phenyl)-ethyl]-amide,
5-chloro-1H-pyrrolo[2,3-c]pyridine-7-carboxylic acid (4-tert-butyl-benzyl)-[2-(3-trifluoromethyl-phenyl)-ethyl]-amide,
7-{(4-tert-butyl-benzyl)-[2-(3,4-dichloro-phenyl)-ethyl]-carbamoyl}-1H-pyrrolo[2,3-c]pyridine-5-carboxylic acid methyl ester,
5-methyl-1H-pyrrolo[2,3-c]pyridine-7-carboxylic acid (4-tert-butyl-benzyl)-{2-[(4-chloro-phenyl)-methyl-amino]-ethyl}-amide, and
5-methyl-1H-pyrrolo[2,3-c]pyridine-7-carboxylic acid butyl-(4-tert-butyl-benzyl)-amide.

6. A compound of claim 1 wherein $R^9$ is 1H-pyrrolo[2,3-c]pyridin-7-yl which is unsubstituted or substituted by one or two substituents independently selected from the group consisting of halogen, $C_1$-$C_6$alkyl, halogen-$C_1$-$C_6$alkyl and C(O)OCH$_3$.

7. A compound of claim 1 wherein $R^9$ is 1H-pyrrolo[2,3-c]pyridin-7-yl which is unsubstituted or substituted by one or two substituents independently selected from the group consisting of methyl, chloro, fluoro, and trifluoromethyl.

8. A compound of claim 1 wherein $R^9$ is 1H-pyrrolo[2,3-c]pyridin-7-yl which is substituted by methyl.

9. A compound of claim 1 wherein $R^9$ is 1H-pyrrolo[2,3-c]pyridin-7-yl which is substituted by fluoro.

10. A compound of claim 1 wherein $R^9$ is 1H-pyrrolo[2,3-c]pyridin-7-yl which is unsubstituted.

11. A compound of claim 1 wherein $R^8$ is phenyl optionally substituted by one or two substituents independently selected from the group consisting of chloro, fluoro, methyl, trifluoromethyl, trifluoromethoxy, and difluoromethoxy.

12. A compound of claim 1 wherein $R^3$ is tert-butyl.

13. A compound of claim 1 selected from the group consisting of:
1H-pyrrolo[2,3-c]pyridine-7-carboxylic acid (4-tert-butyl-benzyl)-[2-(4-fluoro-3-trifluoromethyl-phenyl)-ethyl]-amide,
1H-pyrrolo[2,3-c]pyridine-7-carboxylic acid (4-tert-butyl-benzyl)-[2-(3-trifluoromethyl-phenyl)ethyl]-amide,
1H-pyrrolo[2,3-c]pyridine-7-carboxylic acid (4-tert-butyl-benzyl)-[2-(3,4-dichloro-phenyl)-ethyl]-amide,
1H-pyrrolo[2,3-c]pyridine-7-carboxylic acid (4-tert-butyl-benzyl)-[2-(4-fluoro-phenyl)-ethyl]-amide,
1H-pyrrolo[2,3-c]pyridine-7-carboxylic acid (4-tert-butyl-benzyl)-(2-p-tolyl-ethyl)-amide,
1H-pyrrolo[2,3-c]pyridine-7-carboxylic acid (4-tert-butyl-benzyl)-[2-(3-trifluoromethoxy-phenyl)-ethyl]-amide,
1H-pyrrolo[2,3-c]pyridine-7-carboxylic acid (4-tert-butyl-benzyl)-[2-(3-chloro-4-fluoro-phenyl)-ethyl]-amide,
1H-pyrrolo[2,3-c]pyridine-7-carboxylic acid (4-tert-butyl-benzyl)-[2-(4-chloro-3-trifluoromethyl-phenyl)-ethyl]-amide,
1H-pyrrolo[2,3-c]pyridine-7-carboxylic acid (4-tert-butyl-benzyl)-[2-(3-fluoro-5-trifluoromethyl-phenyl)-ethyl]-amide,
1H-pyrrolo[2,3-c]pyridine-7-carboxylic acid (4-tert-butyl-benzyl)-phenethyl-amide,
5-methyl-1H-pyrrolo[2,3-c]pyridine-7-carboxylic acid (4-tert-butyl-benzyl)-[2-(4-fluoro-phenyl)-ethyl]-amide,
5-methyl-1H-pyrrolo[2,3-c]pyridine-7-carboxylic acid (4-tert-butyl-benzyl)-(2-p-tolyl-ethyl)-amide, 5-methyl-1H-pyrrolo[2,3-c]pyridine-7-carboxylic acid (4-tert-butyl-benzyl)-[2-(3-trifluoromethoxy-phenyl)-ethyl]-amide, 5-methyl-1H-pyrrolo[2,3-c]pyridine-7-carboxylic acid (4-tert-butyl-benzyl)-[2-(4-chloro-3-trifluoromethyl-phenyl)-ethyl]-amide, and 1H-pyrrolo[2,3-c]pyridine-7-carboxylic acid (4-tert-butyl-benzyl)-[2-(3-difluoromethoxy-phenyl)-ethyl]-amide.

14. A compound of claim 1 selected from the group consisting of:

5-methyl-1H-pyrrolo[2,3-c]pyridine-7-carboxylic acid (4-tert-butyl-benzyl)-[2-(3-chloro-4-fluoro-phenyl)-ethyl]-amide, 5-methyl-1H-pyrrolo[2,3-c]pyridine-7-carboxylic acid (4-tert-butyl-benzyl)-[2-(3-fluoro-5-trifluoromethyl-phenyl)-ethyl]-amide, 5-methyl-1H-pyrrolo[2,3-c]pyridine-7-carboxylic acid (4-tert-butyl-benzyl)-phenethyl-amide, 5-methyl-1H-pyrrolo[2,3-c]pyridine-7-carboxylic acid (4-tert-butyl-benzyl)-[2-(3-difluoromethoxy-phenyl)-ethyl]-amide, 5-methyl-1H-pyrrolo[2,3-c]pyridine-7-carboxylic acid (4-tert-butyl-benzyl)-[2-(4-fluoro-3-trifluoromethyl-phenyl)-ethyl]-amide, 5-methyl-1H-pyrrolo[2,3-c]pyridine-7-carboxylic acid (4-tert-butyl-benzyl)-[2-(3-trifluoromethyl-phenyl)-ethyl]-amide, 4-fluoro-1H-pyrrolo[2,3-c]pyridine-7-carboxylic acid (4-tert-butyl-benzyl)-[2-(4-chloro-3-trifluoromethyl-phenyl)-ethyl]-amide, 5-trifluoromethyl-1H-pyrrolo[2,3-c]pyridine-7-carboxylic acid (4-tert-butyl-benzyl)-[2-(4-chloro-3-trifluoromethyl-phenyl)-ethyl]-amide, 4-fluoro-1H-pyrrolo[2,3-c]pyridine-7-carboxylic acid (4-tert-butyl-benzyl)-[2-(4-fluoro-3-trifluoromethyl-phenyl)-ethyl]-amide, 4-fluoro-1H-pyrrolo[2,3-c]pyridine-7-carboxylic acid (4-tert-butyl-benzyl)-[2-(3-trifluoromethyl-phenyl)-ethyl]-amide, 4-fluoro-1H-pyrrolo[2,3-c]pyridine-7-carboxylic acid (4-tert-butyl-benzyl)-[2-(3,4-dichloro-phenyl)-ethyl]-amide, 4-fluoro-1H-pyrrolo[2,3-c]pyridine-7-carboxylic acid (4-tert-butyl-benzyl)-[2-(3-trifluoromethoxy-phenyl)-ethyl]-amide, 4-fluoro-1H-pyrrolo[2,3-c]pyridine-7-carboxylic acid (4-tert-butyl-benzyl)-(2-p-tolyl-ethyl)-amide, 5-trifluoromethyl-1H-pyrrolo[2,3-c]pyridine-7-carboxylic acid (4-tert-butyl-benzyl)-[2-(4-fluoro-3-trifluoromethyl-phenyl)-ethyl]-amide, and 5-trifluoromethyl-1H-pyrrolo[2,3-c]pyridine-7-carboxylic acid (4-tert-butyl-benzyl)-[2-(3-trifluoromethyl-phenyl)-ethyl]-amide.

15. A compound of claim 1 selected from the group consisting of:

5-trifluoromethyl-1H-pyrrolo[2,3-c]pyridine-7-carboxylic acid (4-tert-butyl-benzyl)-[2-(3,4-dichloro-phenyl)-ethyl]-amide, 5-trifluoromethyl-1H-pyrrolo[2,3-c]pyridine-7-carboxylic acid (4-tert-butyl-benzyl)-[2-(3-trifluoromethoxy-phenyl)-ethyl]-amide, 5-trifluoromethyl-1H-pyrrolo[2,3-c]pyridine-7-carboxylic acid (4-tert-butyl-benzyl)-(2-p-tolyl-ethyl)-amide, 4-methyl-1H-pyrrolo[2,3-c]pyridine-7-carboxylic acid (4-tert-butyl-benzyl)-[2-(3,4-dichloro-phenyl)-ethyl]-amide, 5-methyl-1H-pyrrolo[2,3-c]pyridine-7-carboxylic acid (4-tert-butyl-benzyl)-[2-(3,4-dichloro-phenyl)-ethyl]-amide, 4-fluoro-1H-pyrrolo[2,3-c]pyridine-7-carboxylic acid (4-tert-butyl-benzyl)-[2-(4-fluoro-phenyl)-ethyl]-amide, 5-chloro-1H-pyrrolo[2,3-c]pyridine-7-carboxylic acid (4-tert-butyl-benzyl)-[2-(3,4-dichloro-phenyl)-ethyl]-amide, 5-chloro-1H-pyrrolo[2,3-c]pyridine-7-carboxylic acid (4-tert-butyl-benzyl)-[2-(4-fluoro-phenyl)-ethyl]-amide, 5-chloro-1H-pyrrolo[2,3-c]pyridine-7-carboxylic acid (4-tert-butyl-benzyl)-[2-(3-trifluoromethoxy-phenyl)-ethyl]-amide, 5-chloro-1H-pyrrolo[2,3-c]pyridine-7-carboxylic acid (4-tert-butyl-benzyl)-[2-(3-trifluoromethyl-phenyl)-ethyl]-amide, 7-{(4-tert-butyl-benzyl)-[2-(3,4-dichloro-phenyl)-ethyl]-carbamoyl}-1H-pyrrolo[2,3-c]pyridine-5-carboxylic acid methyl ester, 5-methyl-1H-pyrrolo[2,3-c]pyridine-7-carboxylic acid (4-tert-butyl-benzyl)-{2-[(4-chloro-phenyl)-methyl-amino]-ethyl}-amide, and 5-methyl-1H-pyrrolo[2,3-c]pyridine-7-carboxylic acid butyl-(4-tert-butyl-benzyl)-amide.

16. A compound of claim 1 which is 5-methyl-1H-pyrrolo[2,3-c]pyridine-7-carboxylic acid (4-tert-butyl-benzyl)-[2-(3,4-dichloro-phenyl)-ethyl]-amide.

17. A pharmaceutical composition comprising a compound according to claim 1 and a pharmaceutically acceptable carrier or adjuvant or mixtures thereof.

18. A pharmaceutical composition comprising a compound according to claim 5 and a pharmaceutically acceptable carrier or adjuvant or mixtures thereof.

* * * * *